(12) United States Patent
Wittorff

(10) Patent No.: US 12,109,312 B2
(45) Date of Patent: *Oct. 8, 2024

(54) ORAL TABLET FOR TASTE MASKING OF ACTIVE INGREDIENTS

(71) Applicant: Fertin Pharma A/S, Vejle (DK)

(72) Inventor: Helle Wittorff, Vejle Ost (DK)

(73) Assignee: Fertin Pharma A/S, Vejle (DK)

( * ) Notice: Subject to any disclaimer, the term of this patent is extended or adjusted under 35 U.S.C. 154(b) by 396 days.

This patent is subject to a terminal disclaimer.

(21) Appl. No.: 17/341,785

(22) Filed: Jun. 8, 2021

(65) Prior Publication Data

US 2021/0290547 A1  Sep. 23, 2021

Related U.S. Application Data

(63) Continuation of application No. 15/982,510, filed on May 17, 2018, now Pat. No. 11,058,641.

(51) Int. Cl.
*A61K 9/20* (2006.01)
*A61K 9/00* (2006.01)
*A61K 31/522* (2006.01)

(52) U.S. Cl.
CPC .......... *A61K 9/2018* (2013.01); *A61K 9/0056* (2013.01); *A61K 9/2077* (2013.01); *A61K 9/2095* (2013.01); *A61K 31/522* (2013.01); *A61K 9/2086* (2013.01)

(58) Field of Classification Search
None
See application file for complete search history.

(56) References Cited

U.S. PATENT DOCUMENTS

| | | | |
|---|---|---|---|
| 4,627,977 | A | 12/1986 | Gaffar et al. |
| 4,820,506 | A | 4/1989 | Kleinberg et al. |
| 5,576,014 | A | 11/1996 | Mizumoto et al. |
| 5,874,068 | A | 2/1999 | Engelman et al. |
| 6,024,981 | A | 2/2000 | Khankari et al. |
| 6,146,661 | A | 11/2000 | Hoshino |
| 6,287,596 | B1 | 9/2001 | Murakami et al. |
| 7,067,149 | B1 | 6/2006 | Chauveau et al. |
| 8,435,542 | B2 | 5/2013 | Manley et al. |
| 8,658,139 | B1 | 2/2014 | Cutler |
| 2003/0022912 | A1 | 1/2003 | Martino et al. |
| 2003/0215502 | A1 | 11/2003 | Pruss et al. |
| 2009/0311320 | A1 | 12/2009 | Oury et al. |
| 2011/0123462 | A1 | 5/2011 | Mordas et al. |
| 2011/0250247 | A1 | 10/2011 | Boghmans et al. |
| 2012/0276199 | A1 | 11/2012 | Bondu et al. |
| 2013/0302387 | A1 | 11/2013 | Pedersen |
| 2014/0328973 | A1 | 11/2014 | Nielsen |
| 2015/0101627 | A1 | 4/2015 | Marshall et al. |
| 2016/0120793 | A1 | 5/2016 | Abdalla et al. |
| 2016/0145203 | A1 | 5/2016 | Gambogi et al. |
| 2018/0140521 | A1 | 5/2018 | Geonnotti et al. |
| 2018/0140554 | A1 | 5/2018 | Wittorff |
| 2018/0140591 | A1 | 5/2018 | Wittorff et al. |

FOREIGN PATENT DOCUMENTS

| | | |
|---|---|---|
| EP | 0413427 | 2/1991 |
| EP | 0497439 | 8/1992 |
| EP | 0913148 | 5/1999 |
| EP | 0922464 | 6/1999 |
| EP | 1369109 | 12/2003 |
| EP | 1709299 | 12/2005 |
| EP | 1738657 A2 | 1/2007 |
| GB | 1526020 | 9/1978 |
| WO | WO9932092 | 7/1999 |
| WO | WO2002102357 | 12/2002 |
| WO | WO2004068964 | 8/2004 |
| WO | WO2005102066 A2 | 11/2005 |
| WO | WO2006063189 | 6/2006 |
| WO | WO2009007768 | 1/2009 |
| WO | WO2009016133 | 2/2009 |
| WO | WO2009080023 | 7/2009 |
| WO | WO2010104563 | 9/2010 |
| WO | WO2012085043 | 6/2012 |
| WO | WO2013125350 | 8/2013 |
| WO | WO2016061486 | 4/2016 |
| WO | WO2018091048 | 5/2018 |
| WO | WO2018091050 | 5/2018 |
| WO | WO2018093501 | 5/2018 |

OTHER PUBLICATIONS

Bolhuis, et al. "Polyols as filler-binders for disintegrating tablets prepared by direct composition", 2009, Drug Development and Industrial Pharmacy, 35(6_: 671-677.

Module. In C.G. Morris (Ed), Academic Press Dictionary of Science and Technology (4th Ed) 1992. [online] Oxford: Elsevier Science & Technology. Retrived Oct. 11, 2018 from http://search.credoreference.com/content/entry/apdst/module/0, 2 pages.

"Sweetpearl", Product Description, Signet Chemical Corporation Pvt. Ltd, 2018 accessed May 13, 2019 from www.signetchem.com/product.aspx?prdid=1044, 1 page.

(Continued)

*Primary Examiner* — David J Blanchard
*Assistant Examiner* — Daniel F Coughlin
(74) *Attorney, Agent, or Firm* — FORGE IP, PLLC

(57) ABSTRACT

An oral tablet for taste masking of active ingredients includes a population of particles and an active ingredient with off-note taste. The population of particles includes directly compressible (DC) and non-directly compressible (non-DC) sugar alcohol particles, the non-DC particles providing the tablet with a plurality of discrete non-DC areas, and the non-DC areas resulting at least partly in induced taste masking of the active ingredient upon mastication of the tablet.

18 Claims, 3 Drawing Sheets

(56) References Cited

OTHER PUBLICATIONS

Ucla, "Vapor Pressure", Illustrated Glossary of Organinc Chemistry, retrieved on Jul. 17, 2019 from http://www.chem.ucla.edu/~harding/IGOC/V/vapor_pressure.html, 2019, 1 page.

Wessel et al, "Potential benefits of chweing gum for the delivery of oral therapeutics and its possible role in oral healthcare", May 2016, Expert Opinion on Drug Delivery, 13:10, 1421-1431, DOI: 10.1080/17425247.2016.1193154; downloaded from http://www.tandfonline.com/doi/full/10.1080/17425247.2016.1193154.

K.K. Makinen, "Comparison of Erythritol and Xylitol Saliva Stimulants in the Control of Dental Plaque and Mutans *Streptococci*", Caries Res 2001, 35:129-135.

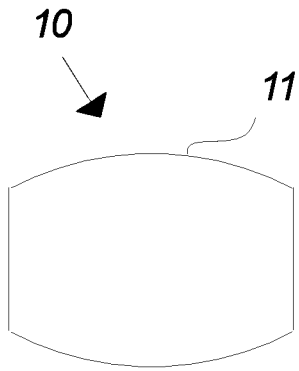
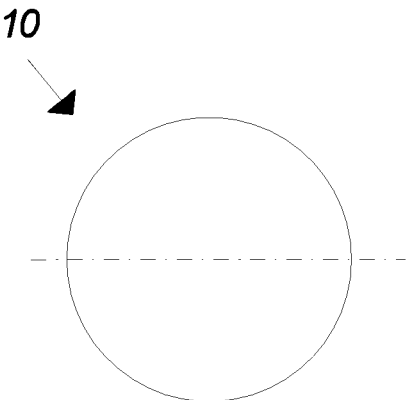
Fig.1a　　　　　Fig.1b
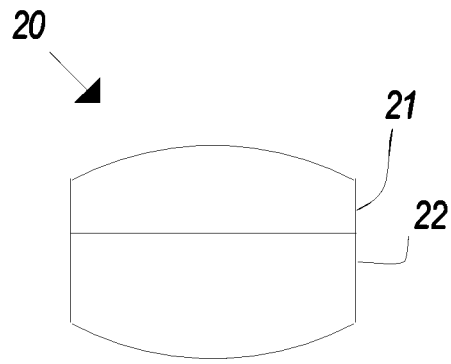
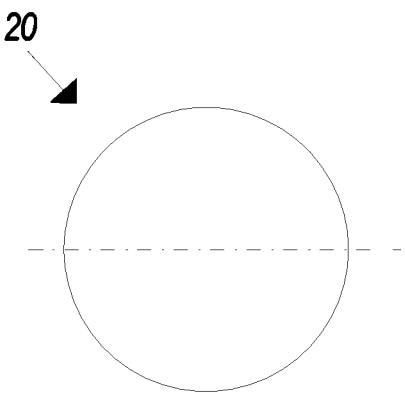
Fig.2a　　　　　Fig.2b
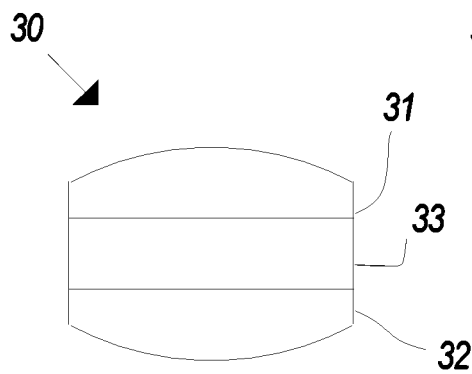
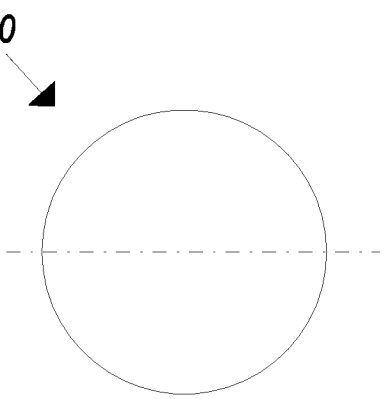
Fig.3a　　　　　Fig.3b

ORAL TABLET FOR TASTE MASKING OF ACTIVE INGREDIENTS

FIELD OF THE INVENTION

The invention relates to a tablet for taste masking of active ingredients, such as active pharmaceutical ingredients.

BACKGROUND OF THE INVENTION

Oral tablets for delivery of active pharmaceutical ingredients are well-known in the art. A challenge in relation to such tablets is that many of such tablets are less than attractive to the user of the tablet. This challenge is significant as users are more and more focused on taste or oral displeasure, and it affects the effectiveness and the options available for such oral tablets. This challenge is in particular relevant in relation to active ingredients with an off-note taste, such as active ingredients with a bitter taste.

SUMMARY OF THE INVENTION

The invention relates to an oral tablet for taste masking of active ingredients, the tablet comprising a population of particles and an active ingredient with off-note taste, the population of particles comprising directly compressible (DC) and non-directly compressible (non-DC) sugar alcohol particles, the non-DC particles providing the tablet with a plurality of discrete non-DC areas, and the non-DC areas resulting at least partly in induced taste masking of the active ingredient upon mastication of the tablet.

According to an embodiment of the invention, non-DC sugar alcohols may effectively mask or compensate unpleasant taste of active ingredients when these active ingredients are released from the tablet during or upon mastication.

It was a surprise to the inventor that it was possible to mask the taste of an active ingredient with an off-note taste by the present invention. It is well-known in the field of pharmaceuticals that active pharmaceutical ingredients are more and less subject to an off-note taste, such as a bitter taste. Accordingly, conventional wisdom in the field of pharmaceuticals has long been that such ingredients are most suitably applied in oral tablets to be swallowed to avoid off-note tastes.

On the other hand, there has been a long felt need in the pharmaceutical industry for means that would allow buccal absorption of active ingredients without such drawbacks. This route of administration is considered to be effective compared to gastrointestinal administration where the active ingredients may and often will be degraded by the liver before they are delivered to their site of action.

Hence, there has been a long felt need in the field of pharmaceuticals for means suitable for buccal absorption of actives that would also be useful in practice. The inventor of the present invention had no expectation of success, and it came as a surprise that the present invention would be a solution to the problems. Also, it was a surprise that the invention is not only applicable for buccal absorption, but may also give some clear benefits for other applications, such as delivery to the throat or gastrointestinal site of action.

According to an advantageous embodiment of the invention, taste masking may thus be obtained through the combined use of a DC sugar alcohol and a non-DC sugar alcohol due to the fact the promoted salivation promoted by the non-DC sugar alcohol establishes a synergy with the DC sugar alcohol as the increased salivation promotes the user's perception to flavor and sweetness.

Taste masking in the present context is broadly referring to conventional sensory understanding within the art of taste, but it further contemplates the effective overall user conception of textural properties, including disintegration and dissolving, during or after mastication. The non-DC sugar alcohols thus establish an overall improved pleasance where the user accepts bad taste or even experience that the taste of the active ingredient is masked in conventional sense.

In the present context, the non-DC sugar alcohol particles are understood and defined by the skilled person with reference to their typical commercial trade grade.

In an advantageous embodiment of the invention the non-DC sugar alcohol particles have not been granulated prior to tableting.

Thus, the non-DC sugar alcohol particles are provided as non-granulated particles.

These are typically available in a non-DC form of the relevant sugar alcohol as particles which have not been preprocessed by granulation with other sugar alcohols or binders for the purpose of obtaining so-called direct compressible particles (DC) on the basis of sugar alcohol particles which are by themselves not suitable for direct compression. Such non-DC particles of sugar alcohol may typically consist of the sugar alcohol. Therefore, non-DC sugar alcohol particles may typically be particles consisting of sugar alcohol, which is non-directly compressible in its pure form. Examples of sugar alcohols which are non-directly compressible when provided as particles consisting of the sugar alcohol in question include erythritol, xylitol, maltitol, mannitol, lactitol, isomalt, etc.

Therefore, preferred non-DC grades of sugar alcohol may include pure sugar alcohol particles.

In an advantageous embodiment of the invention the active ingredient with off-note taste is an active ingredient with an unpleasant taste.

In an advantageous embodiment of the invention the active ingredient with off-note taste is an active ingredient with bitter taste.

In an advantageous embodiment of the invention the active ingredient with off-note taste is an active ingredient with metallic taste.

In an advantageous embodiment of the invention the active ingredient with off-note taste is an active ingredient with astringent taste.

In an advantageous embodiment of the invention the active ingredient with off-note taste is an active ingredient with chalky taste.

In an advantageous embodiment of the invention the active ingredient with off-note taste is an active ingredient with salty taste.

In an advantageous embodiment of the invention the active ingredient with off-note taste is selected from analgesics such as ibuprofen or paracetamol; dextromethorphan; ampicillin; clarithromycin; metronidazole; loperamide; caffeine; sumatriptan and ascorbic acid.

Examples of off-taste active ingredients include bitter tasting active ingredients.

In an advantageous embodiment of the invention the active ingredient is caffeine.

According to an embodiment of the invention, the tablet comprises caffeine as an active ingredient in combination with at least one further active ingredient.

In an advantageous embodiment of the invention said non-DC areas resulting at least partly in induced taste masking of the active ingredient upon mastication of the tablet during at least the first 20 seconds after onset of mastication.

Thus, in the above embodiment the off-note taste is taste masked for a period of at least 20 seconds from onset of mastication. The off-note taste may or may not thereafter be taste masked, however, the period where the off-note taste would be most significant in a conventional chewable tablet would then still be taste masked.

According to an embodiment of the invention the off-note taste is taste masked at least during the first 60 second after onset of mastication.

In an advantageous embodiment of the invention said non-DC areas result at least partly in induced taste masking of the active ingredient upon mastication of the tablet, whereby the tablet provides a pleasant sensation to a user upon mastication.

In an advantageous embodiment of the invention the active ingredient is selected from active ingredients for the throat selected from acetylcysteine, ambroxol, amylmetacresol, benzocaine, bisacodyl, bismuth subsalicylate, bromhexine, cetirizine, cetylpyridinium, chlorhexidine, dextromethorphan hydrobromide, 2,4-dichlorobenzyl alcohol, doxylamine succinate, eucalyptus oil, flurbiprofen, glycerin, hexylresorcinol, lidocaine, menthol, myrrh, paracetamol, pectin, peppermint oil, phenol, phenylephrine, povidone-iodine, pseudoephedrine, ranitidine, simethicone, sodium docusate, spearmint, zinc, or any combination thereof; active ingredients for the gastrointestinal tract selected from alginate, atenolol, aspirin (acetylsalicylic acid), ampicillin, aminosalicylates, anhydrous citric acid, aspirin, bisacodyl, bismuth subsalicylate, bupropion, caffeine, calcium, calcium carbonate, cetirizine, cimetidine, cisapride, clarithromycin, desloratadine, dexlansoprazole, diphenhydramine HCl, diphenhydramine citrate, dimenhydrinate, docusate erythromycin, dopamine, esomeprazole, famotidine, fexofenadine HCl, guaifenesin, hydrotalcite, ibuprofen, ketoprofen, lactase enzyme, lansoprazole, loratadine, lorcaserin, loperamide, loperamide HCl, magnesium, magnesium carbonate, magnesium hydroxide, melatonin, methamphetamine HCl, metoclopramide, metronidazole, montelukast, mycostatin, naltrexone, naproxen, naproxen sodium, nizatidine, omeprazole, ondansetron, orlistat, pantoprazole, paracetamol (acetaminophen), pectin, phentermine HCl, polypodium leucotomos, prednisolone, prednisone, progesterone, propranolol, propantheline bromide, pseudoephedrine HCl, phentermine, rabeprazole, ranitidine, roflumilast, scopoloamine butyl hydroxide, simethicone, sodium, sodium bicarbonate, sodium docusate, sumatriptan, testosterone, tetracycline, topiramate, vitamin A, vitamin B, vitamin B12, vitamin C (ascorbic acid), vitamin D, and vitamin E, vitamin K, or any combination thereof, and active ingredients for buccal absorption selected from atenolol, baclofen, caffeine, carvedilol, chlorpheniramine, chlorpheniramine maleate, fluticasone propionate, maleate, desmopressin, diltiazem hydrochloride, doxylamine succinate, mycostatin, nicotine, nifedipine, nitroglycerin, omeprazole, ondansetron, oxymetazoline HCl, oxytocin, phenylephrine, piroxicam, prednisone, propranolol, salbutamol sulphate, scopoloamine butyl hydroxide, sumatriptan, triamcinolonacetonid, and any combination thereof.

In an advantageous embodiment of the invention the active ingredient is an analgesic.

Examples of analgesics include e.g. ibuprofen, paracetamol (acetaminophen), ketoprofen, aspirin (acetylsalicylic acid), and naproxen.

In an advantageous embodiment of the invention the active ingredient is an anesthetic.

In an advantageous embodiment of the invention the active ingredient is an anti-inflammation agent.

In an advantageous embodiment of the invention the active ingredient is a disinfectant.

In an advantageous embodiment of the invention the active ingredient is a GI stimulant.

Examples of GI stimulants include e.g. metoclopramide, cisapride, and docusate.

In an advantageous embodiment of the invention the active ingredient is a GI relaxant.

Examples of GI relaxants include e.g. loperamide and simethicone.

In an advantageous embodiment of the invention the active ingredient is an antibiotic.

Examples of antibiotics include e.g. ampicillin, erythromycin, tetracycline, clarithromycin, penicillin, and metronidazole.

In an advantageous embodiment of the invention the active ingredient is selected from vitamins, minerals, and supplements (VMS).

Examples of vitamins, minerals, and supplements include e.g. vitamin A, vitamin B, vitamin B12, vitamin C, vitamin D, vitamin E, vitamin K.

In an advantageous embodiment of the invention the active ingredient is a hormone. Examples of hormones include e.g. progesterone, testosterone, and melatonin.

In an advantageous embodiment of the invention the active ingredient is a steroid.

Examples of steroids include e.g. prednisolone and prednisone.

In an advantageous embodiment of the invention the active ingredient is a proton pump inhibitor.

Examples of proton pump inhibitors include e.g. rabeprazole, pantoprazole, esomeprazole, dexlansoprazole, lansoprazole, and omeprazole.

In an advantageous embodiment of the invention the active ingredient is an antihistamine.

Examples of antihistamines include e.g. cimetidine, ranitidine, famotidine, nizatidine, and desloratadine.

Antihistamines are drugs to treat allergic rhinitis and other allergies. Antihistamines can give release to a person with nasal congestion, sneezing or hives caused by e.g. pollen, dust mites or animal allergy.

In an advantageous embodiment of the invention the active ingredient is a triptan.

Examples of triptans include e.g. sumatriptan.

In an advantageous embodiment of the invention the active ingredient is a xerostomia mitigation agent, such as a xerostomia mitigation agent for cancer patients.

In an advantageous embodiment of the invention the active ingredient is a migraine treatment agent.

In an advantageous embodiment of the invention the active ingredient is an enzyme.

One advantage of enzymes may be that digestion may be accelerated and/or that intestinal balance is restored or improved.

In an advantageous embodiment of the invention the active ingredient is a gastrointestinal medication.

In this context a gastrointestinal medication is understood as an active ingredient acting in the gastrointestinal tract.

In an advantageous embodiment of the invention the active ingredient is an opioid.

In an advantageous embodiment of the invention the tablet is a medical device for alleviating or treating dysphagia by inducing saliva generation.

In an advantageous embodiment of the invention the active ingredient is an allergy medication.

In one embodiment, the active ingredient is an allergy medication for buccal absorption. One advantage of such embodiment is that immediate action may be obtained by bypassing the digestive system thereby bypassing the liver.

In another embodiment, the active ingredient is an allergy medication for gastrointestinal delivery and uptake.

In an advantageous embodiment of the invention the active ingredient is a cough and cold agent.

In an advantageous embodiment of the invention the active ingredient is cetirizine.

In an advantageous embodiment of the invention the active ingredient is bromhexine.

In an advantageous embodiment of the invention the active ingredient is cetylpyridinium.

In an advantageous embodiment of the invention the active ingredient is chlorhexidine.

In an advantageous embodiment of the invention the active ingredient is amylmetacresol.

In an advantageous embodiment of the invention the active ingredient is paracetamol.

In an advantageous embodiment of the invention the active ingredient is ibuprofen.

In an advantageous embodiment of the invention the active ingredient is omeprazole.

In an advantageous embodiment of the invention the active ingredient is ondansetron.

In an advantageous embodiment of the invention the active ingredient is esomeprazole.

In an advantageous embodiment of the invention the active ingredient is rantidine.

In an advantageous embodiment of the invention the active ingredient is nicotine In an advantageous embodiment of the invention the active ingredient is chlorpheniramine.

In an advantageous embodiment of the invention the active ingredient is oxytocin.

In an advantageous embodiment of the invention the active ingredient is desmopressin.

In an advantageous embodiment of the invention the active ingredient is prednisone.

In an advantageous embodiment of the invention the active ingredient is diphenhydramine.

In an advantageous embodiment of the invention the active ingredient is benzydaminhydrochlorid.

In an advantageous embodiment of the invention the active ingredient is penicillin.

In an advantageous embodiment of the invention the tablet is designed to release at least 50% by weight of the active ingredient within 20 seconds from onset of mastication.

In an advantageous embodiment of the invention the tablet is designed to provide fast onset action of the active ingredient.

In an advantageous embodiment of the invention the tablet further comprises a saliva production inhibiting agent for controlling saliva production.

In an advantageous embodiment of the invention the tablet is designed to release the active ingredient in the oral cavity for absorption through the oral mucosa of a part of the active ingredient, wherein the tablet is designed to deliver a part of the active ingredient to the throat as part of saliva generated upon mastication of the tablet, and wherein the tablet is designed to deliver a part of the active ingredient to the gastrointestinal tract.

In an advantageous embodiment of the invention the tablet comprises means for sustained release.

In an advantageous embodiment of the invention the active ingredient is at least partly encapsulated.

In an advantageous embodiment of the invention the active ingredient is a prodrug.

In an advantageous embodiment of the invention the part of the active ingredient absorbed through the oral mucosa results in fast onset action of the active ingredient.

In an advantageous embodiment of the invention the part of the active ingredient delivered to the gastrointestinal tract results in sustained action of the active ingredient.

In an advantageous embodiment of the invention the tablet is designed to release the active ingredient in the oral cavity for absorption through the oral mucosa of a part of the active ingredient, and wherein the tablet is designed to deliver another part of the active ingredient to the throat as part of saliva generated upon mastication of the tablet.

In an advantageous embodiment of the invention the tablet is designed to deliver a part of the active ingredient to the throat as part of saliva generated upon mastication of the tablet, and wherein the tablet is designed to deliver another part of the active ingredient to the gastrointestinal tract.

In an advantageous embodiment of the invention the tablet is designed to release the active ingredient in the oral cavity for absorption through the oral mucosa of a part of the active ingredient, and wherein the tablet is designed to deliver another part of the active ingredient to the gastrointestinal tract as part of saliva generated upon mastication of the tablet.

In an advantageous embodiment of the invention the part of the active ingredient absorbed through the oral mucosa results in fast onset action of the active ingredient.

In an advantageous embodiment of the invention the part of the active ingredient delivered to the gastrointestinal tract results in sustained action of the active ingredient.

In an advantageous embodiment of the invention the active ingredient is an active pharmaceutical ingredient.

According to an embodiment of the invention, the active pharmaceutical ingredient is included in the second population of particles.

In an advantageous embodiment of the invention the tablet comprises flavor in an amount of 1-10% by weight of the tablet.

According to an embodiment of the invention, the tablet comprises flavor in an amount of 1-6% by weight of the tablet, such as 2-6% by weight of the tablet.

Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), chili, cinnamon redhots, cotton candy, circus cotton candy, clove, coconut, coffee, clear coffee, double chocolate, energy cow, ginger, glutamate, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof. In an embodiment of the invention the flavor is a powder flavor.

In an embodiment of the invention the tablet comprises a first module comprising the population of particles, the first module comprising at least a portion of the flavor.

In an embodiment of the invention the tablet comprises a second module comprising a second population of particles, the second module comprising at least a portion of the flavor.

In an advantageous embodiment of the invention the tablet is designed to release at least 50% by weight of the flavor within 20 seconds from onset of mastication.

According to an embodiment of the invention the tablet is designed to turn into liquid within 20 seconds from onset of mastication.

According to an embodiment of the invention, the oral tablet is designed to turn into liquid within 20 seconds from onset of in vivo chewing, where the in vivo chewing is carried out by a chewing panel comprising at least 10 individuals, chewing at a rate of 60 chews per minute.

In the present context, the above reference to turning into a liquid refers to a user perception. This fast turning into liquid as perceived by the user is highly preferable as it facilitates a desirable mouthfeel.

According to an embodiment of the invention the tablet is designed to dissolve within 20 seconds from onset of mastication.

According to an embodiment of the invention, the oral tablet is designed to dissolve within 20 seconds from onset of in vivo chewing, where the in vivo chewing is carried out by a chewing panel comprising at least 10 individuals, chewing at a rate of 60 chews per minute.

In an advantageous embodiment of the invention said population of particles is tableted into a first module and combined with a second population of particles that is tableted into a second module.

Thus, a synergy between utilization of non-DC sugar alcohol particles as a disintegration promoter due to the lower mechanical strength and also as a salivation promoter in combination with a second module, which can provide additional mechanical strength, thereby acting as a carrier module. This is especially advantageous when the second population of particles contributes to an attractive mouthfeel by a high content of DC sugar alcohols, which also provides mechanical strength to the tablet.

One advantage of the above embodiment may be that the second module may have a higher mechanical strength, e.g. by means of a different composition comprising e.g. a very large amount of direct compressible ingredients, such as DC sugar alcohols.

A further advantage of the above embodiment may be that the second module may have a higher loading capacity for e.g. active ingredients, partly due to the higher obtainable mechanical strength achievable by large amounts of direct compressible ingredients, such as DC sugar alcohols.

Thus, in the above embodiment said population of particles is tableted into a first module, and wherein the tablet further comprises a second population of particles that is tableted into a second module. The first module may be tableted before the second module, or vice versa. In some embodiments, the tablet may comprise one or more further modules.

In an embodiment of the invention the oral tablet comprises at least two modules. A tablet comprising two or more modules will have module sizes which each are comparable to the volume of the complete tablet. Comparable in the present context means that the modules are not understood as small particles and a module should at least be greater than $\frac{1}{20}$ of the complete tablet volume, preferably greater than $\frac{1}{10}$ of the complete tablet volume.

The module may typically be gathered from a plurality of compressed particles and have a weight which is greater than 0.2 gram and less than 10 grams.

In an embodiment of the invention a module is defined as a plurality of particles being compressed together to form a gathered module of particles.

In an embodiment of the invention the oral tablet comprises a plurality of oral tablet modules. In the present context the application of e.g. two modules are in particular advantageous as the use of non-DC sugar alcohols by nature may result in a more fragile tablet or at least the module in which the non-DC sugar alcohols are. In other words, non-DC sugar alcohols may be present primarily in one module thereby optimizing the desired salivation and sensory experience from the module and the tablet as such whereas another module may serve as a support ensuring that the desired mechanical stability/shelf life/friability of the complete tablet is obtained.

In an embodiment of the invention the plurality of modules are slice-like layers. The term "slice-like" layer is a plain but very precise way of to the skilled person how a module may be provided, as such a layer is a standard structure obtained through conventional tableting procedures.

According to an embodiment of the invention, the tablet has two modules. Optionally, a coating may be applied around the two modules to form the final tablet.

An advantage of using two modules is described above, but it should also be noted that this effect may also be obtained when applying layers of very different nature. Such application may e.g. include the use of a gum module and a non-gum module, where the non-gum modules are containing the non-DC sugar alcohol particles. In this way, the non-gum layer may release the advantageous non-DC sugar alcohols and the gum layer may both stabilize the tablet as described above but also interact with the non-DC sugar alcohols during in particular the initial release for establishment of a very pleasant and impressing initial chew phase. This includes an increased saliva and moisture experience.

In an embodiment of the invention, the active ingredient is included in the second population of particles.

In an embodiment of the invention said population of particles is tableted into a first module and combined with a second population of particles that is tableted into a second module, where the second population of particles is different from the first population of particles.

In an embodiment of the invention said population of particles is tableted into a first module and combined with a second population of particles that is tableted into a second module, where the second population of particles is different from the first population of particles, where the second population of particles is free of non-DC sugar alcohols.

In one embodiment, the second population of particles comprises a large amount of DC sugar alcohols, such as larger amounts than the first population of particles. For example, the second population of particles may comprise at least 30% by weight of DC sugar alcohols, such as at least 50%, such as at least 70% by weight of sugar alcohols. In an example embodiment, the second population of particles may comprise between 50 and 99.9% by weight of sugar alcohols, such as between 70 and 99% by weight of sugar alcohols. The amount of DC sugar alcohol applied may depend on the type and amount of active ingredient applied in the tablet.

In an embodiment of the invention the second module is tableted before the first module.

In an advantageous embodiment of the invention the non-DC areas are evenly distributed in the tablet or at least one module of the tablet.

One advantage of the above embodiment may be that the even distribution of the non-DC areas promotes an effective disintegration of the module upon mastication, e.g. due to lower mechanical strength contribution from the non-DC particles, thereby facilitating effective contacting of the resulting mastication fragments formed by the mastication with saliva, again increasing dissolving of the tablet. Also, the even distribution of the non-DC areas promotes a high number of mastication fragments with non-DC sugar alcohols, which again effectively promotes salivation. Thus, a synergy between utilization of non-DC sugar alcohol particles as a disintegration promoter due to the lower mechanical strength and also as a salivation promoter in combination with the even distribution to facilitate effect dispersion of mastication fragments in the oral cavity upon mastication.

In an advantageous embodiment of the invention a series of at least 10 of said tablets comprises said non-DC particles in an amount varying with a relative standard deviation (RSD) below 10%.

One advantage of the above embodiment may be that uniform product may be obtained having low variation in the amount of non-DC sugar alcohol between tablets. Consequently, the functionality provided by non-DC areas in the tablet may provide low variation between tablets.

It is noted that the reference to RSD and a sequence of tablets typically refers to a tablet series of a production line.

Furthermore, the RSD of the non-DC sugar alcohol between tablets is a measure of the degree of even distribution of the non-DC areas. Therefore, having an RSD below 10% in a series of at least 10 tablets indicates an even distribution of the non-DC areas. Having evenly distributed non-DC areas facilitates a high salivation since the non-DC areas are effectively distributed in the mouth upon mastication and a resulting disintegration of the tablet.

According to an embodiment of the invention, the amount of non-DC particles between a series of at least 10 of the tablets holds a relative standard deviation (RSD) below 5%.

An advantageous method of dosing non-DC sugar alcohols into a composition for a large number of tablets has been established, which facilitates an exact dosing of the non-DC sugar alcohols in a series of tablets. This means that large-scale production of tablets comprising non-DC sugar alcohols is made possible with improved results concerning distribution of the non-DC areas in the tablets and thereby an improved RSD between the tablets of a series.

The term RSD as used herein is short for the relative standard deviation, which within this present field is used to indicate the uniformity in content of non-DC sugar alcohols in a series of tablets. An analysis may be carried out on an array of 10 tablets of a series, wherein the content of the non-DC sugar alcohols in question is measured. From these values the RSD may be calculated through the standard formula of RSD=(standard deviation of array X)*100%/(average of array X).

In some cases, it may be most convenient to measure RSD of the amount of non-DC sugar alcohol particles indirectly. For example, the RSD of another ingredient may be used as an indicator for the amount of non-DC sugar alcohol particles, as segregation affects the whole composition of the tablet or module in question.

When attempting to obtain a high degree of even distribution of the non-DC areas, insufficient mixing may lead to uneven distribution, such as undesirable agglomeration of particles within certain parts of the tablet. Also, even if mixing very thoroughly the ingredients, an undesirable handling of the mixture from the mixing to a tableting machine may lead to segregation. For example, smaller particles may typically segregate to the bottom part of a container, thereby leading to different particle distributions for different tablets. Particularly when the different ingredients have different particle sizes, e.g. if non-DC particles have a larger particle size compared to other ingredients, segregation may lead to different contents of non-DC sugar alcohols in different tablets. Yet, another aspect is that even storing a thoroughly mixed composition for too long may lead to segregation.

On the other hand, a measure of having obtained even distribution of non-DC areas in at least one module of the tablet may be that a series of at least 10 of the tablets holds a relative standard deviation (RSD) below 10% with respect to the non-DC sugar alcohol content.

In is noted that the term segregation as used herein would be known to the skilled person to mean the separation of a mixture according to similarity, typically size. This may in the present context be a problem when handling a mixture comprising very different sizes of particles, e.g. in a hopper for holding and feeding the composition via a feeding mechanism to a die cavity.

Particularly when including active ingredients in the tablet, having a low RSD on the content of such active ingredients is highly desirable.

In an advantageous embodiment of the invention the non-DC areas are homogenously distributed in the tablet or at least one module of the tablet.

One advantage of the above embodiment may be that the homogenous distribution of the non-DC areas promotes an effective disintegration of the module upon mastication, e.g. due to lower mechanical strength contribution from the non-DC particles, thereby facilitating effective contacting of the resulting mastication fragments formed by the mastication with saliva, again increasing dissolving of the tablet. Also, the homogenous distribution of the non-DC areas promotes a high number of mastication fragments with non-DC sugar alcohols, which again effectively promotes salivation. Thus, a synergy between utilization of non-DC sugar alcohol particles as a disintegration promoter due to the lower mechanical strength and also as a salivation promoter in combination with the homogenous distribution to facilitate effect dispersion of mastication fragments in the oral cavity upon mastication.

In an advantageous embodiment of the invention the active ingredient is included in the second population of particles.

According to an embodiment of the invention, the active ingredient is included in the first population of particles.

According to an embodiment of the invention, the active ingredient is present in the first population of particles and in the second population of particles. Thus, in that embodiment the total amount of active ingredient may be obtained by combining the first and the second populations of particles.

In an advantageous embodiment of the invention the first and the second modules each comprise an amount of the active ingredient, where the amount of active ingredient in the second module is higher than in the first module. In this way, the module with the highest amount of active ingredient may act as a mechanical support to the first module.

In an embodiment of the invention, the active ingredient is comprised in the second module. Thus, in that embodiment the first module is free of the active ingredient.

In an advantageous embodiment of the invention the tablet is a chewable tablet.

In an advantageous embodiment of the invention at least 10% by weight of said population of particles have a particles size below 250 μm, and wherein at least 30% by weight of said population of particles have a particles size above 500 μm.

According to an embodiment of the invention, the population of particles have a particle size distribution with a full width at half maximum (FWHM) of at least 100 μm.

Particularly when having a broad particle size distribution of the population of particles, it was surprising to the inventor that even distribution of the non-DC areas could be accomplished. Typically, when having a broad particle size distribution, such as when having a width from the 10% quantile to the 90% quantile greater than 30% of the mean value, associated compositions are considered vulnerable to segregation. However, according to an embodiment of the invention, the non-DC areas are evenly distributed in at least one module of the tablet and may have amounts of non-DC particles between a series of at least 10 of the tablets holding a relative standard deviation (RSD) below 10%.

According to an embodiment of the invention, the non-DC particles have an average non-DC particle size at least 50 μm larger than an average DC particle size of the DC particles.

In an advantageous embodiment of the invention the non-DC sugar alcohol particles are selected from non-DC particles of erythritol, maltitol, xylitol, isomalt, lactitol, mannitol, and combinations thereof.

One advantage of the above embodiment may be that a desirable induced saliva generation is obtained.

According to an embodiment of the invention, the non-DC sugar alcohol particles consist of sugar alcohols selected from erythritol, maltitol, xylitol, isomalt, lactitol, mannitol, and combinations thereof.

In an advantageous embodiment of the invention the non-DC sugar alcohol particles are selected from non-DC particles of erythritol, maltitol, xylitol, isomalt, and combinations thereof.

One advantage of the above embodiment may be that a desirable induced saliva generation is obtained.

In an advantageous embodiment of the invention the non-DC sugar alcohol particles are selected from non-DC particles of erythritol, maltitol, xylitol, and combinations thereof.

One advantage of the above embodiment may be that a desirable induced saliva generation is obtained. Also, when a cooling sensation is desirable, having non-DC sugar alcohol particles comprising or consisting of erythritol, xylitol, or combinations thereof advantageous.

In an advantageous embodiment of the invention the non-DC sugar alcohol particles are non-DC erythritol particles.

One advantage of the above embodiment may be that a desirable induced saliva generation is obtained, together with a cooling sensation.

In an advantageous embodiment of the invention the non-DC sugar alcohol particles are non-DC xylitol particles.

One advantage of the above embodiment may be that a desirable induced saliva generation is obtained, together with a cooling sensation.

In an advantageous embodiment of the invention the tablet comprises said non-DC sugar alcohol particles in an amount of at least 10% by weight of the tablet.

In an advantageous embodiment of the invention said DC sugar alcohol particles comprises sugar alcohols selected from DC particles of sorbitol, erythritol, xylitol, lactitol, maltitol, mannitol, isomalt, and combinations thereof.

Sorbitol is an example of a sugar alcohol, which is considered DC grade, when provided as particles consisting of sorbitol, i.e. in its pure form. On the other hand, several other sugar alcohols are considered non-DC grade if providing them as particles consisting of the specific sugar alcohol. Therefore, such non-DC sugar alcohols are conventionally processed into DC grade sugar alcohols, e.g. by granulating them with e.g. a binder.

Examples of trade grades of DC sugar alcohols include sorbitol particles provided as e.g. Neosorb® P 300 DC from Roquette, mannitol particles provided as e.g. Pearlitol® 300DC or Pearlitol 200 SD from Roquette, maltitol provided as e.g. SweetPearl® P 300 DC, xylitol provided as e.g. Xylisorb® 200 DC or Xylitab 200 from Dupont.

In an advantageous embodiment of the invention the tablet comprises said DC sugar alcohol particles in an amount of at least 10% by weight of the tablet.

According to an embodiment of the invention, said population of particles comprises DC sugar alcohol particles in an amount of at least 10% by weight.

According to an embodiment of the invention, the first module comprises DC sugar alcohol particles in an amount of at least 10% by weight.

In an advantageous embodiment of the invention the second module comprises DC sugar alcohol particles in an amount of at least 30% by weight of the second module.

In an advantageous embodiment of the invention the second module comprises DC sugar alcohol particles in an amount of at least 50% by weight of the second module.

In an embodiment of the invention the DC sugar alcohol particles in the second module are selected from DC particles of sorbitol, erythritol, xylitol, lactitol, maltitol, mannitol, isomalt, and combinations thereof.

In an advantageous embodiment of the invention friability of the tablet is less than 3%, such as less than 2%, such as less than 1.5%, wherein friability is measured according to European Pharmacopoeia 9.1, test method 2.9.7. by using a pharmaceutical friability-tester PTF 10E from Pharma Test.

One advantage of the above embodiment may be that a tablet with a relatively high mechanical stability is obtained, while at the same time having the desirable mouthfeel of the invention.

According to an embodiment of the invention, friability of the tablet is between 0.2% and 3%, such as between 0.2% and 2%, wherein friability is measured according to European Pharmacopoeia 9.1, test method 2.9.7. by using a pharmaceutical friability-tester PTF 10E from Pharma Test.

In an advantageous embodiment of the invention the tablet comprises one or more binders other than binders forming part of the DC sugar alcohol particles in an amount of 0.1 to 6% by weight of the tablet.

Suitable binders include Gum Arabic, Methyl Cellulose, Liquid glucose, Tragacanth, Ethyl Cellulose, Gelatin, Hydroxy Propyl Methyl Cellulose (HPMC), Starches, Hydroxy Propyl Cellulose (HPC), Pregelatinized Starch, Sodium Carboxy Methyl Cellulose (NaCMC), Alginic Acid, Polyvinyl Pyrrolidone (PVP), Maltodextrine (MD); Cellulose, Polyethylene Glycol (PEG), Polyvinyl Alcohols, Polymethacrylates, Copovidone or Microcrystalline Cellulose (MCC), alone or in combination.

According to an embodiment of the invention, the one or more binders comprises one or more cellulose binders.

In an embodiment of the invention the one or more binders comprises microcrystalline cellulose (MCC), hydroxypropyl cellulose (HPC) or hydroxypropylmethyl cellulose (HPMC) or any combination thereof.

In an embodiment of the invention the oral tablet comprises hydroxypropyl cellulose (HPC) binder in the amount of 0.1 to 6% by weight of the tablet, such as 0.1 to 5%, such as 0.1 to 4%, such as 0.1 to 3%, such as 0.1 to 2% by weight of the tablet.

HPC may be applied as a particular attractive binder. Thus, this binder, when used with non-DC sugar alcohols such as erythritol, exhibits an advantageous sensory experience when compared to other well-known binders. In particular, the user of HPC lower than 4% by weight of the tablet is advantageous, such as 0.1 to 3%, such as 0.1 to 2% by weight of the tablet.

In an embodiment of the invention the non-DC sugar alcohol particles are particles that are not granulated, and the one or more binders are present as separate components in the tablet.

In an embodiment of the invention the non-DC sugar alcohol particles are particles consisting of the sugar alcohol and the particles are not pre-granulated together with the one or more binders that are present in the tablet as separate components. It is noted that the use of binders as particles separate from the non-DC particles does not compromise the advantageous sensory properties even when applying a firm pressure tableting force, whereas the granulation with the binder to the sugar alcohol clearly reduces the desired sensory properties.

In an advantageous embodiment of the invention the resistance to crunching of the tablet is greater than 60N, such as greater than 70N, such as greater than 80N, such as greater than 90N, such as greater than 100 N, such as greater than 110, such as greater than 130N such as greater than 150N, wherein the resistance to crunching of the tablet is less than 300N, such as less than 250N, such as less than 200N, wherein the resistance to crunching is determined according to European Pharmacopoeia 9.1, test method 2.9.8. by using a pharmaceutical resistance to crunching tester model Pharma Test type PTB 311.

According to an embodiment of the invention, the tablet comprises at least one module, the module comprising more than 10% by weight of compressed non-DC sugar alcohol particles, the resistance to crunching of the module being greater than 60N, such as greater than 70N, such as greater than 80N, such as greater than 90N such as greater than 100 N, where the resistance to crunching is determined according to the European Pharmacopoeia 9.1, test method 2.9.8. by using a pharmaceutical resistance to crunching tester model Pharma Test type PTB 311.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the formulation.

In an advantageous embodiment of the invention the tablet has a weight ratio between said non-DC sugar alcohol particles and said DC sugar alcohol particles, which is between 0.3 and 0.7.

The weight ratio between non-DC sugar alcohol particles and DC sugar alcohol particles have proven significant according to an embodiment of the invention in the sense that a relatively high amount of non-DC sugar alcohol particles must be present in order to obtain the mouthfeel and taste obtained through the invention. However, this taste and mouthfeel also resides in the DC sugar alcohol particles. An example of such DC sugar alcohol particle is DC grade xylitol, which, together with the non-DC sugar alcohol particles may provide a mouthfeel which is unique and very attractive to test panels.

The weight ratio between non-DC sugar alcohol particles and DC sugar alcohol particles have proven significant as mentioned above in relation to the direct sensation and mouthfeel experienced by the user but is has moreover addressed the challenge in relation to mouthfeel when DC sugar alcohol particles crumbles during the initial chew. The mechanical stability of the tablet is much desired when the tablet is in its non-chewed form, but a fast disintegration and dissolving is desirable when the tablet is chewed due to the fact that user of the tablet dislike a sandy mouthfeel induced through small hard-pressed crumbles of DC sugar alcohol. The use of a very high amount of non-DC sugar alcohol particles will facilitate a perceived fast dissolving and disintegration of the tablet after the initial chews.

According to an embodiment of the invention the tablet has a weight ratio between said non-DC sugar alcohol particles and said DC sugar alcohol particles, which is greater than 0.3, such as greater than 0.4, such as greater than 0.5.

According to an embodiment of the invention the tablet has a weight ratio between said non-DC sugar alcohol particles and said DC sugar alcohol particles, which is smaller than 0.7, such as smaller than 0.6, such as smaller than 0.55.

The weight ratio between non-DC sugar alcohol particles and DC sugar alcohol particles is important for the purpose of obtaining an advantageous taste and mouthfeel. By having an upper limit of this weight ratio, the chewer will moreover also experience a desirable crunch sensation when starting masticating the tablet, the crunch being obtained through the use of substantial amounts of DC sugar alcohol particles and the non-DC sugar alcohol particles.

According to an embodiment of the invention, the tablet comprises the non-DC sugar alcohol particles in an amount of greater than 0.3 gram.

According to an embodiment of the invention, the weight of non-DC sugar alcohol particles contained in the tablet is greater than greater than 0.4 gram, such as greater than 0.5 gram, such as greater than 0.6 gram, such as greater than 0.7 gram, such as greater than 0.8 gram, such as greater than 0.9 gram, such as greater than 1.0 gram.

According to a further embodiment of the invention, the amount of non-DC sugar alcohol particles is relatively high. It is in particular high when considering that the non-DC sugar alcohol in conventional sense is not regarded attractive for compression, but the mouthfeel and salivation perceived by the user is there improved significantly, when compared to low amounts or the same amounts of DC sugar alcohol.

According to an embodiment of the invention, the tablet comprises the non-DC sugar alcohol particles in an amount of less than 3.0 gram, such as less than 2.0 gram, such as less than 1.5 gram.

In an embodiment of the invention wherein the tablet has a weight of between 0.5 and 4.0 grams.

In an advantageous embodiment of the invention the non-DC areas results in induced saliva generation.

In an advantageous embodiment of the invention saliva generation upon mastication of the tablet is induced compared to a tablet without non-DC sugar alcohol particles.

In an advantageous embodiment of the invention saliva generation upon mastication of the tablet is induced compared to a tablet where the discrete areas are based on DC sugar alcohol particles.

In an advantageous embodiment of the invention the tablet generates more than 1.5 mL saliva within 30 seconds from onset of mastication.

According to an embodiment of the invention the discrete non-DC areas induces saliva generation of more than 2.0 mL saliva within 30 seconds from onset of mastication.

According to an embodiment of the invention the discrete non-DC areas induces saliva generation of more than 3.0 mL saliva within 30 seconds from onset of mastication.

In an advantageous embodiment of the invention the tablet generates more than 1.5 mL saliva within a period from 30 to 90 seconds from onset of mastication.

According to an embodiment of the invention the discrete non-DC areas induces saliva generation of more than 2.0 mL saliva within the period from 30 to 90 seconds from onset of mastication.

In an advantageous embodiment of the invention the tablet generates more than 1.5 mL saliva within a period from 90 to 180 seconds from onset of mastication.

In an advantageous embodiment of the invention the tablet generates more than 1.5 mL saliva within a period from 180 to 300 seconds from onset of mastication.

In an advantageous embodiment of the invention the tablet comprises particles comprising gum base, and wherein the tablet is designed to be masticated into a coherent residual containing water-insoluble components.

The application of gum may in the present context may invoke a delay of release for active ingredients and this may again promote the buccal and upper throat absorption of active pharmaceutical ingredient when this is released from the oral tablet during mastication.

In an advantageous embodiment of the invention the oral tablet contains particles comprising gum base, and wherein the gum base comprises at least 5% by weight of elastomer.

The specific use of a relatively high proportion of elastomer in the gum base may effectively be used for modification of the release of active ingredients in terms of time and amount and the elastomer may also provide robust structure of the tablet facilitating that it is chewed into a coherent residual containing water-insoluble components. Some active ingredient may risk invoking disintegration of the residual whereas an elastomer may increase the coherence and compensate for the aggressive active ingredients.

In an embodiment of the invention the gum base comprises at least 10% by weight of elastomer.

In an embodiment of the invention the gum base comprises at least 15% by weight of elastomer.

In an embodiment of the invention the gum base comprises between 15% and 25% by weight of elastomer.

In an embodiment of the invention the gum base comprises between 17% and 23% by weight of elastomer.

In an advantageous embodiment of the invention the tablet is free of gum base.

The invention further relates to an oral tablet suitable for taste masking of active ingredients, the tablet comprising a population of particles, the population of particles comprising directly compressible (DC) and non-directly compressible (non-DC) sugar alcohol particles, the tablet being designed to turn into liquid within 20 seconds of mastication.

The invention further relates to an oral tablet suitable for taste masking of active ingredients, the tablet comprising a population of particles, the population of particles comprising directly compressible (DC) and non-directly compressible (non-DC) sugar alcohol particles, the tablet being designed to dissolve within 20 seconds of mastication.

According to an advantageous embodiment of the invention the oral tablet according to any of the two aforementioned embodiments is composed according to the invention or any of its embodiments.

The invention further relates to a method of providing induced taste masking, the method comprising the steps of:
i) providing an oral tablet comprising a population of particles and an active ingredient with off-note taste, the population of particles comprising directly compressible (DC) and non-directly compressible (non-DC) sugar alcohol particles, and
ii) masticating the tablet and thereby at least partly generating taste masking in the oral cavity induced by a plurality of discrete non-DC areas in the tablet.

In an advantageous embodiment of the invention step ii) of masticating the tablet involves releasing at least 50% by weight of the active ingredient within 20 seconds from onset of mastication.

In an advantageous embodiment of the invention the method of the invention or any of its embodiments involves providing the tablet of the invention or any of its embodiments.

THE FIGURES

The invention will now be described with reference to the drawings where

FIGS. 1a and 1b shows an embodiment of the invention,

FIGS. 2a and 2b shows a two-module version of an embodiment of the invention,

FIGS. 3a and 3b shows a three-module version of an embodiment of the invention,

DETAILED DESCRIPTION

Figure 4:
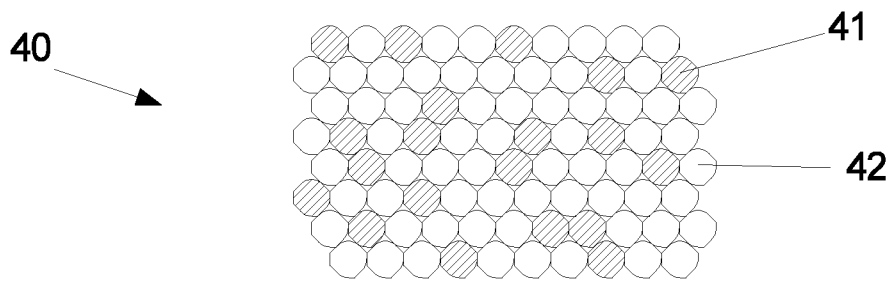
FIGS. 4 and 5 illustrates embodiments of the invention

As used herein the term "oral tablet" is considered as a tablet for oral use. Particularly, the oral tablet is considered as formed by tableting, i.e. compression of a particle composition, comprising the mentioned population of particles. Thus, the tablet is considered a compressed tablet formed by a plurality of particles. Typically, the oral tablet may also be referred to as a tablet.

In the present context the phrase "population of particles" refers to a statistical population of particles. The population of particles may be characterized by a number of different parameters, e.g. statistical parameters such as distribution of particles, average particle size, particle size distribution width, etc. The population of particles may have subpopulations, such as DC sugar alcohol particles, non-DC sugar alcohol particles, or in some embodiments particles comprising gum base. The phrasing "population of particles" may in an embodiment of the invention be provided as a plurality of tableted particles and where the population of particles are tableted in one module or it may refer to a population of particles where some of the particles are tableted into one module and other particles are tableted into another module.

In the present context, the term "non-DC areas" refers to small volumes or spaces formed during tableting from the non-DC particles of non-DC sugar alcohol. Moreover, each of the non-DC areas may be composed of a single non-DC sugar alcohol particle, or may comprise several non-DC sugar alcohol particles. When the non-DC areas are distinct, i.e. not diffuse, the non-DC areas may be evenly distributed in the tablet, or at least one module thereof when the tablet comprises two or more modules. In such embodiments, where the non-DC areas are evenly distributed in in the tablet, or at least one module thereof, the non-DC areas may thus facilitate an even saliva generation in the mouth upon mastication.

The term "non-DC sugar alcohol particles" refer to particles of non-directly compressible (non-DC) sugar alcohol. It is noted that the terms "non-DC sugar alcohol particles" and "non-DC particles" are used interchangeably. In the present context, the non-DC sugar alcohol particles refer to particles which have not been preprocessed by granulation with e.g. other sugar alcohols or binders for the purpose of obtaining so-called direct compressible particles (DC). Thus, non-DC sugar alcohol particles are considered as particles consisting of non-DC sugar alcohol.

The term "DC sugar alcohol particles" refer to particles of direct compressible (DC) sugar alcohol. It is noted that the terms "DC sugar alcohol particles" and "DC particles" are used interchangeably. DC sugar alcohol particles may be obtained e.g. as particles of sugar alcohols having DC grade by nature, e.g. sorbitol, or by granulating non-DC sugar alcohol with e.g. other sugar alcohols or binders for the purpose of obtaining so-called direct compressible particles (DC).

In the present context, the term "taste masking" refers broadly to masking of any sensations perceived as unpleasant or other off-note tastes, but not necessarily confined to the classical five basic tastes. A typical example of off-note taste includes bitter taste. Also, metallic taste is another example of as an off-note taste.

In the present context when the non-DC areas are referred to as "discrete" this signifies that the non-DC sugar alcohols are not continuously distributed, but present in the discrete areas corresponding to the discrete nature of the non-DC sugar alcohol particles.

When referring to induced saliva generation, it is noted that this induced saliva generation exceeds any saliva generation without the use of the tablet of the invention. Particularly, in an embodiment the induced saliva generation exceeds saliva generation when using conventional tablets without non-DC areas. Then, induced saliva generation is increased over any saliva generation associated with conventional products, e.g. by comparing with a tablet without non-DC sugar alcohol particles, or with a tablet where the discrete areas are based on DC sugar alcohol particles.

When referring to induced saliva generation, the saliva generation is tested using the following method.

Test subject abstain from eating and drinking at least 30 minutes before initiation of any test. Immediately before introducing of the tablet into the oral cavity, the test subject swallows. The test subject refrains from swallowing during the test. Immediately after introducing of the tablet into the oral cavity, the test subject starts masticating the tablet at a frequency of 1 chew per second for 20 seconds. Then, saliva and any remains of the tablet is kept in the mouth within chewing for 10 second. 30 seconds after starting the test, the test subject discards saliva including any tablet fragments into a plastic cup, which is weighted. Saliva discarded also at 90 seconds after onset of mastication, at 180 seconds after onset of mastication, at 300 seconds after onset of mastication, at 420 seconds after onset of mastication, and at 600 seconds after onset of mastication. At all times, the test subject makes as little movement as possible, and refrains from swallowing.

As used herein, the term "particle size" refers to the average particle size as determined according to European Pharmacopoeia 9.1 when using test method 2.9.38 particle size distribution estimation by analytical sieving, unless otherwise specifically is mentioned.

In the present context, the term "taste masking" refers broadly to masking of any sensations perceived as unpleasant or otherwise off-note tastes, but not necessarily confined to the classical five basic tastes. A typical example of off-note taste includes bitter taste. Also, metallic taste is another example of as an off-note taste.

As used herein the term "active ingredient" refers to a substance that is biologically active and has a physiological effect on the human body for the benefit of the human body or part thereof. Active ingredients include active pharmaceutical ingredients, but also other active substances such as nutraceuticals.

In the present context the term "release" refers to the released substance being liberated from the water-soluble matrix. In some embodiments, the process of releasing a substance corresponds to the substance being dissolved in saliva.

As used herein the term "buccal absorption" refers to a substance diffusing across the oral mucosa from the oral cavity to enter the bloodstream.

As used herein the term "oral mucosa" refers to the mucous membrane in the oral cavity, i.e. in the mouth.

As used herein the term "gastrointestinal tract" refers to the part of the digestive system starting with the stomach and ending with the anus, including the intestines. Thus, the mouth and esophagus are not considered part of the gastrointestinal tract for the purposes of the present application.

As used herein the term "throat" is considered front part of the neck, positioned in front of the vertebra, and including the pharynx and larynx.

In the following raw materials will refer to the mixed particles to be compressed into a tablet according to embodiments of the invention unless otherwise stated.

The following description outlines explanations of how the tablet of the invention may be produced and further details of what may be added to the inventive composition.

Typically, the process of manufacture of the inventive tablet may be performed in a single tablet press, such as a rotary tablet press. But it may be a benefit under some circumstances to apply a separate tablet press.

Preferably, the upper punch is convex which gives the upper face of the pressed tablet a concave form.

It should of course be noted that the shape of the punches may vary depending of the desired tablet shape.

In some embodiments of the invention, pressing of the tablets are performed at a force of 20 to 50 kN.

Important raw materials of the inventive tablet are non-DC sugar alcohol particles in combination with DC sugar alcohol particles.

The DC sugar alcohol particles refer to sugar alcohols known within the art as being direct compressible (DC).

The non-DC sugar alcohol particles refer to sugar alcohols known within the art as being non-directly compressible (DC).

According to a further embodiment of the invention, the applied non-DC sugar alcohol particles are best characterized as being non-directly compressible (non-DC). The use of non-DC sugar alcohols when compared to conventionally applied direct compressible sugar alcohol (DC) has shown remarkable effects to the user's perception of the delivery vehicle when chewed. This may partly be due to the somewhat larger size of non-DC sugar alcohol, when compared to DC sugar alcohol, but is may also be a result of a high content of sugar alcohol in the individual particles applied for compression. DC sugar alcohols, which for obvious reasons are marketed and applied for compression purposes, does not result in such improved salivation effect and mouthfeel.

It should be noted that the terminology non-DC is easily understood within the field of technology. Suppliers or sugar alcohol provides clear guidance to the user as for the ability for use in relation to compression of tablets. A non-DC particle in this connection is referred to as a particle which is not expressly recommended by the supplier for compression. Examples of a non-DC grade of erythritol includes Zerose™ erythritol 16952F supplied by Cargill. Further examples of non-DC sugar alcohol particles include non-DC xylitol as Xivia C from Dupont, non-DC isomalt as Isomalt GS from Beneo Paltinit, non-DC mannitol as Pearlitol from Roquette, non DC maltitol as Maltisorb. P200 from Roquette. Examples of a direct compressible (DC) grade of erythritol include Zerose™ DC 16966 also supplied by Cargill. Further examples of DC sugar alcohols include sorbitol particles provided as e.g. Neosorb® P 300 DC from Roquette, mannitol particles provided as e.g. Pearlitol® 300DC or Pearlitol 200 SD from Roquette, maltitol provided as e.g. SweetPearl® P 300 DC, xylitol provided as e.g. Xylisorb® 200 DC or Xylitab from Dupont.

Non-direct compressible (non-DC) sugar alcohols may include non-DC grades of Xylitol, non-DC grades of Erythritol, non-DC grades of Mannitol, non-DC grades of maltitol, non-DC grades of Lactitol, non-DC grades of Isomalt, or other suitable non-DC grades of sugar alcohols.

Direct compressible (DC) sugar alcohols may include sorbitol which is DC by nature, DC grades of Xylitol, DC grades of Erythritol, DC grades of Mannitol, DC grades of maltitol, DC grades of Lactitol, Isomalt or other suitable DC grades of sugar alcohols.

The present invention benefits from a synergy between the non-DC sugar alcohol particles and the DC sugar alcohol particles. The DC sugar alcohols may be e.g. sorbitol which is direct compressible by nature or it may be other sugar alcohols which has been preprocessed, e.g. by granulation with a suitable binder, to obtain particles which when compressed may encapsulate the non-DC sugar alcohol particles into a mechanically stable tablet. At the same time the non-DC sugar alcohol particles serves as a means for salivation which is both attractive to the user and also serves for the purpose of dissolving the DC sugar alcohol particles when the tablet is chewed as fast as possible.

According to embodiments of the invention, encapsulated flavors or active ingredients may be added to the final blend of raw materials prior to compression.

Different methods of encapsulating flavors or active ingredients, which may both refer to flavors or active ingredients mixed into the raw materials to be compressed into the chewing gum may e.g. include spray drying, spray cooling, film coating, coascervation, Double emulsion method (Extrusion technology) or prilling.

Materials to be used for the above-mentioned encapsulation methods may e.g. include Gelatine, Wheat protein, Soya protein, Sodium caseinate, Caseine, Gum arabic, Mod. starch, Hydrolyzed starches (maltodextrines), Alginates, Pectin, Carregeenan, Xanthan gum, Locus bean gum, Chitosan, Bees wax, Candelilla wax, Carnauba wax, Hydrogenated vegetable oils, Zein and/or Sucrose.

Preferably, these ingredients should be added subsequent to any significant heating or mixing. In other words, the active ingredients should preferably be added immediately prior to the compression of the final tablet.

If applying the present invention in relation to chewing gum, the adding of active ingredients may be cautiously blended with pre-mixed gum base granulates and further ingredients such as the ingredients stipulated by the present claims, immediately prior to the final compression of the tablet.

In the present context, the oral tablet may include different types of active ingredients to be taste masked. A number of these are listed below. It should however be stressed that only active ingredients listed below with an off-note taste or unpleasant taste are within the scope of the present invention.

In one embodiment the tablet according to the invention comprises a pharmaceutically, cosmetically or biologically active substance. Examples of such active substances, a comprehensive list of which is found e.g. in WO 00/25598, which is incorporated herein by reference, include drugs, dietary supplements, antiseptic agents, pH adjusting agents, anti-smoking agents and substances for the care or treatment of the oral cavity and the teeth such as hydrogen peroxide and compounds capable of releasing urea during chewing. Examples of useful active substances in the form of antiseptics include salts and derivatives of guanidine and biguanidine (for instance chlorhexidine diacetate) and the following types of substances with limited water-solubility; quaternary ammonium compounds (e.g. ceramine, chloroxylenol, crystal violet, chloramine), aldehydes (e.g. paraformaldehyde), derivatives of dequaline, polynoxyline, phenols (e.g. thymol, p-chlorophenol, cresol), hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. also Martindale, The Extra Pharmacopoeia, 28th edition, pages 547-578; metal salts, complexes and compounds with limited water-solubility, such as aluminum salts, (for instance aluminum potassium sulphate AlK(SO4)2, 12H2O) and salts, complexes and compounds of boron, barium, strontium, iron, calcium, zinc, (zinc acetate, zinc chloride, zinc gluconate), copper (copper chloride, copper sulphate), lead, silver, magnesium, sodium, potassium, lithium, molybdenum, vanadium should be included; other compositions for the care of mouth and teeth: for instance; salts, complexes and compounds containing fluorine (such as sodium fluoride, sodium monofluorophosphate, aminofluorides, stannous fluoride), phosphates, carbonates and selenium. Further active substances can be found in J. Dent. Res. Vol. 28 No. 2, pages 160-171, 1949.

Examples of active substances in the form of agents adjusting the pH in the oral cavity include: acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulphates or oxides of sodium, potassium, ammonium, magnesium or calcium, especially magnesium and calcium.

Active ingredients may comprise the below mentioned compounds or derivates thereof but are not limited thereto: Acetaminophen, Acetylsalicylic acid, Buprenorphine, Bromhexin, Celcoxib, Codeine, Diphenhydramineiclofenac, Etoricoxib, Ibuprofen, Indometacin, Ketoprofen, Lumiracoxib, Morphine, Naproxen, Oxycodon, Parecoxib, Piroxicam, Pseudoefedrin, Rofecoxib, Tenoxicam, Tramadol, Valdecoxib, Calciumcarbonat, Magaldrate, Disulfiram, Bupropion, Nicotine, Azithromycin, Clarithromycin, Clotrimazole, Erythromycin, Tetracycline, Granisetron, Ondansetron, Prometazin, Tropisetron, Brompheniramine, Ceterizin, leco-Ceterizin, Chlorcyclizine, Chlorpheniramin, Chlorpheniramin, Difenhydramine, Doxylamine, Fenofenadin, Guaifenesin, Loratidin, des-Loratidin, Phenyltoloxamine, Promethazin, Pyridamine, Terfenadin, Troxerutin, Methyldopa, Methylphenidate, Benzalcon. Chloride, Benzeth. Chloride, Cetylpyrid. Chloride, Chlorhexidine, Ecabet-sodium, Haloperidol, Allopurinol, Colchinine, Theophylline, Propanolol, Prednisolone, Prednisone, Fluoride, Urea, Actot, Glibenclamide, Glipizide, Metformin, Miglitol, Repaglinide, Rosiglitazone, Apomorfin, Cialis, Sildenafil, Vardenafil, Diphenoxylate, Simethicone, Cimetidine, Famotidine, Ranitidine, Ratinidine, cetrizin, Loratadine, Aspirin, Benzocaine, Dextrometorphan, Phenylpropanolamine, Pseudoephedrine, Cisapride, Domperidone, Metoclopramide, Acyclovir, Dioctylsulfosucc., Phenolphtalein, Almotriptan, Eletriptan, Ergotamine, Migea, Naratriptan, Rizatriptan, Sumatriptan, Zolmitriptan, Aluminum salts, Calcium salts, Ferro salts, Ag-salts, Zinc-salts, Amphotericin B, Chlorhexidine, Miconazole, Triamcinolonacetonid, Melatonine, Phenobarbital, Caffeine, Benzodiazepiner, Hydroxyzine, Meprobamate, Phenothiazine, Buclizine, Brometazine, Cinnarizine, Cyclizine, Difenhydramine, Dimenhydrinate, Buflomedil, Amphetamine, Caffeine, Ephedrine, Orlistat, Phenylephedrine, Phenylpropanolamin, Pseudoephedrine, Sibutramin, Ketoconazole, Nitroglycerin, Nystatin, Progesterone, Testosterone, Vitamin B12, Vitamin C, Vitamin A, Vitamin D, Vitamin E, Pilocarpin, Aluminumaminoacetat, Cimetidine, Esomeprazole, Famotidine, Lansoprazole, Magnesiumoxide, Nizatide and or Ratinidine.

The invention is suitable for increased or accelerated release of active agents selected among the group of dietary supplements, oral and dental compositions, antiseptic agents, pH adjusting agents, anti-smoking agents, sweeteners, flavorings, aroma agents or drugs. Some of those will be described below.

The active agents to be used in connection with the present invention may be any substance desired to be released from the tablet. The active agents, for which a controlled and/or accelerated rate of release is desired, are primarily substances with a limited water-solubility, typically below 10 g/100 mL inclusive of substances which are totally water-insoluble. Examples are medicines, dietary supplements, oral compositions, anti-smoking agents, highly potent sweeteners, pH adjusting agents, flavorings etc.

Other active ingredients are, for instance, paracetamol, benzocaine, cinnarizine, menthol, carvone, caffeine, chlorhexidine-di-acetate, cyclizine hydrochloride, 1,8-cineol, nandrolone, miconazole, mystatine, sodium fluoride, nicotine, cetylpyridinium chloride, other quaternary ammonium compounds, vitamin E, vitamin A, vitamin D, glibenclamide or derivatives thereof, progesterone, acetylsalicylic acid, dimenhydrinate, cyclizine, metronidazole, sodium hydrogen carbonate, the active components from ginkgo, the active components from propolis, the active components from ginseng, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, folic acid, niacine, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutritionists accepted by the authorities in different countries such as for instance US code of Federal Regulations, Title 21, Section 182.5013.182 5997 and 182.8013-182.8997.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, pages 547-578; metal salts, complexes and compounds with limited water-solubility, such as aluminum salts, (for instance aluminum potassium sulphate AlK(SO4) 2, 12H2O) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodiummonofluorophosphate, amino fluorides, stannous fluoride), phosphates, carbonates and selenium.

Cf. furthermore J. Dent. Res. Vol. 28 No. 2, pages 160-171, 1949, wherein a wide range of tested compounds is mentioned.

Examples of active agents in the form of agents adjusting the pH in the oral cavity include for instance: acceptable acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

Further examples of active agents are medicines of any type.

Examples of active agents in the form of medicines include caffeine, salicylic acid, salicyl amide and related substances (acetylsalicylic acid, choline salicylate, magnesium salicylate, sodium salicylate), paracetamol, salts of pentazocine (pentazocine hydrochloride and pentazocine-lactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedinpine as well as suitable substances and salts thereof mentioned in Pharm. Int., November 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase, glucoseoxidase, streptokinase, streptodornase, dextranase, alpha amylase), polypeptides (oxytocin, gonadorelin, (LH.RH), desmopressin acetate (DDAVP), isoxsuprine hydrochloride, ergotamine compounds, chloroquine (phosphate, sulfate), isosorbide, demoxytocin, heparin.

Other active ingredients include beta-lupeol, Letigen®, Sildenafil citrate and derivatives thereof.

Further examples of active ingredients include dental products including Carbamide, CPP Caseine Phospho Peptide; Chlorhexidine, Chlorhexidine di acetate, Chlorhexidine Chloride, Chlorhexidine di gluconate, Hexetedine, Strontium chloride, Potassium Chloride, Sodium bicarbonate, Sodium carbonate, Fluor containing ingredients, Fluorides, Sodium fluoride, Aluminum fluoride.

Further examples of active ingredients include Ammonium fluoride, Calcium fluoride, Stannous fluoride, Other fluor containing ingredients Ammonium fluorosilicate, Potassium fluorosilicate, Sodium fluorosilicate, Ammonium monofluorphosphate, Calcium monofluorphosphate, Potassium monofluorphosphate, Sodium monofluorphosphate, Octadecentyl Ammonium fluoride, Stearyl Trihydroxyethyl Propylenediamine Dihydrofluoride Further examples of active ingredients include vitamins. Vitamins include A, B1, B2, B6, B12, Folinic acid, Folic acid, niacin, Pantothenic acid, biotine, C, D, E, K. Minerals include Calcium, phosphor, magnesium, iron, Zinc, Copper, Iod, Mangan, Crom, Selene, Molybden. Other active ingredients include:

Q10R, enzymes. Natural drugs including *Ginkgo Biloba*, ginger, and fish oil.

Further examples of active ingredients include migraine drugs such as Serotonin antagonists: Sumatriptan, Zolmitriptan, Naratriptan, Rizatriptan, Eletriptan; nausea drugs such as Cyclizin, Cinnarizin, Dimenhydramin, Difenhydrinat; hay fever drugs such as Cetrizin, Loratidin, pain relief drugs such as Buprenorfin, Tramadol, oral disease drugs such as Miconazol, Amphotericin B, Triamcinolonaceton; and the drugs Cisaprid, Domperidon, Metoclopramid. In a preferred embodiment the invention relates to the release of Nicotine and its salts.

In an advantageous embodiment of the invention the active ingredient is selected from active ingredients for the throat selected from acetylcysteine, ambroxol, amylmetacresol, benzocaine, bisacodyl, bismuth subsalicylate, bromhexine, cetirizine, cetylpyridinium, chlorhexidine, dextromethorphan hydrobromide, 2,4-dichlorobenzyl alcohol, doxylamine succinate, eucalyptus oil, flurbiprofen, glycerin, hexylresorcinol, lidocaine, menthol, myrrh, paracetamol, pectin, peppermint oil, phenol, phenylephrine, povidone-iodine, pseudoephedrine, ranitidine, simethicone, sodium docusate, spearmint, zinc, or any combination thereof; active ingredients for the gastrointestinal tract selected from alginate, atenolol, aspirin (acetylsalicylic acid), ampicillin, aminosalicylates, anhydrous citric acid, aspirin, bisacodyl, bismuth subsalicylate, bupropion, caffeine, calcium, calcium carbonate, cetirizine, cimetidine, cisapride, clarithromycin, desloratadine, dexlansoprazole, diphenhydramine HCl, diphenhydramine citrate, dimenhydrinate, docusate erythromycin, dopamine, esomeprazole, famotidine, fexofenadine HCl, guaifenesin, hydrotalcite, ibuprofen, ketoprofen, lactase enzyme, lansoprazole, loratadine, lorcaserin, loperamide, loperamide HCl, magnesium, magnesium carbonate, magnesium hydroxide, melatonin, methamphetamine HCl, metoclopramide, metronidazole, montelukast, mycostatin, naltrexone, naproxen, naproxen sodium, nizatidine, omeprazole, ondansetron, orlistat, pantoprazole, paracetamol (acetaminophen), pectin, phentermine HCl, polypodium leucotomos, prednisolone, prednisone, progesterone, propranolol, propantheline bromide, pseudoephedrine HCl, phentermine, rabeprazole, ranitidine, roflumilast, scopoloamine butyl hydroxide, simethicone, sodium, sodium bicarbonate, sodium docusate, sumatriptan, testosterone, tetracycline, topiramate, vitamin A, vitamin B, vitamin B12, vitamin C (ascorbic acid), vitamin D, and vitamin E, vitamin K, or any combination thereof, and active ingredients for buccal absorption selected from atenolol, baclofen, caffeine, carvedilol, chlorpheniramine, chlorpheniramine maleate, fluticasone propionate, maleate, desmopressin, diltiazem hydrochloride, doxylamine succinate, mycostatin, nicotine, nifedipine, nitroglycerin, omeprazole, ondansetron, oxymetazoline HCl, oxytocin, phenylephrine, piroxicam, prednisone, propranolol, salbutamol sulphate, scopoloamine butyl hydroxide, sumatriptan, triamcinolonacetonid, and any combination thereof.

In a further embodiment, the sucrose fatty acid esters may also be utilized for increased release of sweeteners including for instance the so-called highly potent sweeteners, such as for instance saccharin, cyclamate, aspartame, thaumatin, dihydrocalcones, stevioside, glycyrrhizin or salts or compounds thereof. For increased released of sweetener, the sucrose fatty acids preferable have a content of palmitate of at least 40% such as at least 50%.

When including gum base in the formulation sugar alcohols typically constitute from about 5 to about 95% by weight of the tablet, more typically about 20 to about 80% by weight such as 30 to 70% or 30 to 60% by weight of the tablet.

In such an embodiment of the invention, the tablet further comprises, beside the already described sugar alcohols, materials selected from the group consisting of bulk sweeteners, flavors, dry-binders, tableting aids, anti-caking agents, emulsifiers, antioxidants, enhancers, absorption enhancers, buffers, high intensity sweeteners, softeners, colors, or any combination thereof.

Suitable sugar alcohols typically constitute from about 40 to about 99.9% by weight of the tablet, such as about 80 to about 99% by weight of the tablet.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the tablet formulation.

A tablet according to the invention may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers and combinations thereof.

FIGS. 1a and 1b illustrates an embodiment of an oral tablet 10 according to an embodiment of the invention. FIG. 1a shows the oral tablet from the side and FIG. 1b shows the tablet from above.

Figure 5:
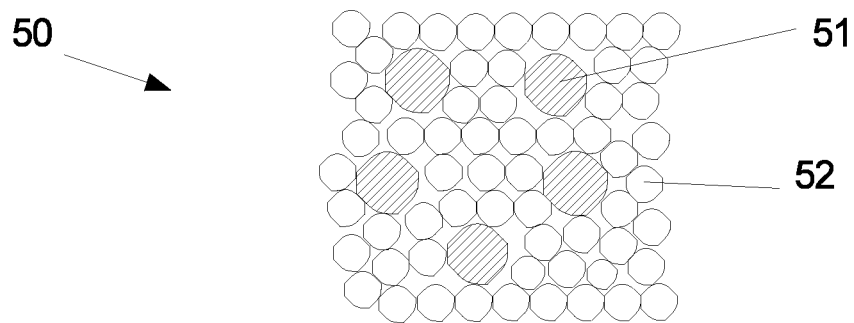

The composition and the way the tablet is or can be made is described elsewhere in the application and details regarding the structure and functioning of this tablet 10 is also indicated and explained further with reference to FIG. 4 and FIG. 5.

FIGS. 2a and 2b illustrates a two-module version of an oral tablet according to an embodiment of the invention. FIG. 2a shows the oral tablet from the side and FIG. 2b shows the tablet from above.

The composition and the way the tablet is made is described elsewhere in the application.

Figure 6:
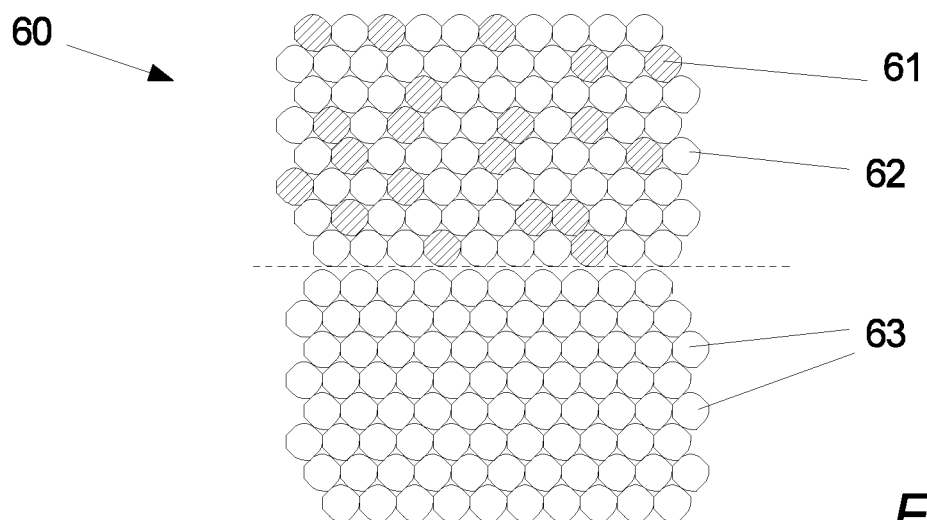
FIG. 6 illustrates a two-module version of an embodiment of the invention and where

Details regarding the structure and functioning of this tablet 10 is also indicated and explained further with reference to FIGS. 4, 5 and 6.

The intention with this illustration is to give an example of a physical form, which may be applicable within the scope of the invention. The intention is also to illustrate how the term "a module" is understood and applied throughout the description, i.e. that a module is referring to a population of a plurality particles and the particles have been tableted together to form a module. The term module is applied to indicate that one module comprises one population of tableted particles and another module comprises another population of tabled particles. A population of particles in the present context is thus understood to refer to a plurality of particles. A singular particle is thus of course not understood as a module.

Modules are typically, but not necessarily, distinguishable by the human eye, in particular if the applied compounds in the different modules are formed by differently colored population of particles or mixtures of particles.

The oral tablet 20 comprises an upper module 21 and a lower module 22. The modules, here in the shapes of layers, are thus physically distinct and each comprises a population of particles which has been tableted. The population of the different modules, 21 and 22, may typically be different for many purposes. Examples include use for visual conception, for mechanical purposes e.g. providing strength, for medical purposes, and of course also for maximizing the desired effect of non-DC sugar alcohol contained in the tablet.

In a preferred embodiment, most of the applied non-DC sugar alcohol(s) is comprised in the upper module 21 and the lower module 22 is mostly comprised of DC-components, i.e. components such as sugar alcohols, fillers, flavors, colors etc. conventionally used for direct compression. In embodiments of the invention, a first module, here the lower module 22 may be regarded and applied as a support module supporting another module, here the upper module 21. The benefit of this division in the designing of properties is that the module containing the non-DC sugar alcohol particles may comprises substantial amounts of non-DC sugar alcohol particles even in spite of the fact that the modules own mechanical strength is substantially weakened, as the supporting modules structural strength may be designed to ensure that the overall structural strength of the tablet is sufficient to obtain the desired friability and tablet appearance. This multi-modular design approach is of even more interest as the tablets designed according to this principle benefits, in terms of disintegration and dissolving of the tablet matrix during mastication of the tablet, from the increased salivation effect obtained from the applied high content of non-DC sugar alcohol particles in the relatively weak module.

FIGS. 3a and 3b illustrates a three-module version of an oral tablet 30 according to an embodiment of the invention. FIG. 3a shows the oral tablet 30 from the side and FIG. 3b shows the tablet from above.

The illustrated tablet 30 comprises an upper module 31, and intermediate module 33 and a lower module 32.

The upper module 31 may, as explained in relation to the upper module of FIGS. 2a and 2b, be formed by a population of particles comprising an effective amount of non-DC sugar alcohol particles. The intermediate layer may comprise further non-DC sugar alcohol particles and or a desired active ingredient.

The lower module 32 may comprise substantial amounts of DC-particles such as sugar alcohol(s), fillers, some binder and other relevant ingredients enabling the lower module 32 to form a structural support for at least the upper module 31.

FIG. 4 illustrates a part 40 of a cross-section of one of the oral tablets in FIG. 1-3. The part of the oral tablet, illustrated in FIG. 4 may thus correspond to a view of a part of the upper layers 21 or 31 or a part of the tablet 1.

Such part 40 of a tablet may within the scope of the invention comprise at least two different types of particles, namely non-DC sugar alcohol particles 41 and DC-particles 42. Preferred but non-limiting non-DC sugar alcohols are non-DC erythritol and non-DC xylitol as these non-DC sugar alcohols have shown effective to obtain the desired effect. The illustrated non-DC particles 41, although indicated on the figures with the same graphical expression may of course comprise non-DC sugar alcohol particles of the same type, but also comprise a mixture of two or more non-DC sugar alcohol particles.

The particles are evenly distributed amongst a plurality of DC particles 42 within the specified module. The DC particles 42, although indicated in the figure as same type particles may include different types of DC sugar alcohol particles, flavor particles, binders, etc. The intention with the figure is to illustrate that the non-DC sugar alcohol particles 41 in practice have to be homogenously distributed amongst the DC particles 42 in the final oral tablet 40. It may not be enough that the non-DC particles and DC particles are mixed homogenously at some stage during the preparation of the tableting process. The homogenous mix should preferably be maintained in the final oral tablet 40 in order to promote the desired effect and to obtain a mechanically stable tablet. A further advantageous effect of the evenly distributed non-DC sugar alcohol particles may be obtained through an advantageous and increased salivation during mastication of a tablet.

The understanding and conception of the evenly distribution of the non-DC sugar alcohol particles in the relevant tablet module may in practical terms be very difficult to define as such definitions are very difficult to monitor and control during the processing of the tablet but it has been possible to establish an industrial scale process, where the mixture containing the substantial amounts of non-DC sugar alcohol(s) may be established all the way through the process into the final tablet. Such process may e.g. be validated by test manufacturing of a sequence of tablets where the variation of the non-DC sugar alcohol content of the manufactured tablets are determined.

It is noted that the non-DC particles 41 forms small sub-areas or sub spaces in the final oral tablet or the relevant module of the final tablet, e.g. the upper modules 21 and 31. These sub-areas are elsewhere in the present application referred to as discrete non-DC areas and may be formed by single non-DC particles or very small groups of these non-DC particles. These discrete non-DC areas are thus intended to be contained within a matrix formed by DC-sugar alcohol particles or other DC-particles.

The non-DC areas, in the present embodiment, the non-DC sugar alcohol particles 41 are thus included in substantial amounts in the tablet and from a mechanical perspective supported and contained by the DC-particles 42 and together forming a matrix which, when chewed, may bring the non-DC sugar alcohol particles 41 into contact with the oral cavity and promote salivation. The promoted salivation, together with relatively weak mechanical structure of the module or tablet comprising the non-DC sugar alcohol particles induces a fast breakup of the tablet and thereby pushes the non-DC particles into contact with the oral cavity in a way which is completely different from compressed tablets made from DC-sugar alcohol particles, such as granulated erythritol or xylitol.

The non-DC areas may thus result in induced saliva generation upon mastication of the tablet and also induce and promote a very fast and pleasant dissolving of the tablet matrix when compared to conventional compressed tablets.

Active ingredients may be present as both DC and non-DC particles as long as the active ingredient as such does not interfere significant with other compounds. If the active ingredients are non-DC particles, the amount should be kept low enough to ensure the mechanical stability of the tablet or modules or alternatively compensated by relevant DC-particles or binders. It should be noted that such a compensation should be carefully considered as this compensation may both compromise salivation effect and texture/mouthfeel during mastication.

FIG. 5 illustrates a part of a cross-section of one of the oral tablets in FIG. 1-3. The part of the oral tablet, illustrated in FIG. 5 may thus correspond a view of a part of the upper modules 21 or 31 or the tablet 1.

In terms of components applied, the tablet part illustrated in FIG. 5 may largely correspond to the above-described embodiment of FIG. 4, but now the tablet part comprises larger sized non-DC particles 51 containing in a compression of particles of DC particles 52.

The intention with the present FIG. 5 is merely to indicate that in particular the non-DC sugar alcohol particles may be larger in size than the DC particles and it is also noted in this context that the use of larger sized non-DC sugar alcohol particles may indeed increase the obtained salivation or the desired effect.

FIG. 6 illustrates a particular transition in a tablet 60 with two adjacent modules according to an embodiment of the invention. The presently illustrated part of such tablet may e.g. refer to the transition between the modules 21 and 22 of the tablet 20 as seen in FIG. 2a. The tablet 60 comprises non-DC sugar alcohol particles 61 and DC particles 62 in one module and another module comprising DC particles 63. The understanding of a module is here easily conceivable as the population of non-DC sugar alcohol particles 61 and DC particles 62 forms one module and the population of DC particles 63 forms another module. Often, the compositions of the DC sugar alcohol particles 62 and the DC sugar alcohol particles 63 may be different, depending on the specific circumstances.

Again, in relation to FIG. 5 and FIG. 6, active ingredients may be present as both DC and non-DC particles as long as the active ingredient as such does not interfere significant with other compounds. If the active ingredients are non-DC particles, the amount should be kept low enough to ensure the mechanical stability of the tablet or modules or alternatively compensated by relevant DC-particles or binders. It should be noted that such a compensation should be carefully considered as this may compensation may both compromise salivation effect and texture/mouthfeel during mastication.

Particles comprising gum base, may also be present both as non-DC and DC particles, although DC-particles comprising gum base are highly preferred over non-DC gum base-containing particles. When applying particles comprising gum base, these particles are preferably but not necessarily included in a supporting module as DC particles 63 e.g. with mixed with sugar alcohol particles 63 as illustrated in FIG. 6.

The above illustrated modules are all designed as layers. It is stressed that other shapes of modules may be applicable within the scope of the invention. Non-limiting examples are modules having a sphere shape, diamond shape, oval shape, cone shape, etc. All the relevant shapes must of course be adapted to fit the tableting process according to known measures within the art.

EXAMPLES

Examples 1-62. Preparation of Two-Layer Tablets

TABLE 1A

Oral tablet compositions for bi-layer tablets containing active ingredients. Amount are given in wt-% of the respective layer of tablet.

| | | Ex. 1 | Ex. 2 | Ex. 3 | Ex. 4 | Ex. 5 | Ex. 6 | Ex. 7 |
|---|---|---|---|---|---|---|---|---|
| First layer (wt %) | Non-DC Erythritol | 50 | 50 | 50 | 50 | 50 | 50 | 50 |
| | DC Isomalt | 43.75 | 43.75 | 43.75 | 43.75 | 43.75 | 43.75 | 43.75 |
| | Flavor | 4 | 4 | 4 | 4 | 4 | 4 | 4 |
| | HIS | 0.25 | 0.25 | 0.25 | 0.25 | 0.25 | 0.25 | 0.25 |
| | Magnesium Stearate | 1 | 1 | 1 | 1 | 1 | 1 | 1 |
| | Binder HPC | 1 | 1 | 1 | 1 | 1 | 1 | 1 |
| Second layer (wt %) | DC Maltitol | 93.75 | 94.55 | 94.749 | 89.75 | 94.74 | 94.25 | 94.25 |
| | DC Xylitol | — | — | — | — | — | — | — |
| | DC Isomalt | — | — | — | — | — | — | — |
| | Flavor | 4 | 4 | 4 | 4 | 4 | 4 | 4 |
| | HIS | 0.25 | 0.25 | 0.25 | 0.25 | 0.25 | 0.25 | 0.25 |
| | Magnesium Stearate | 1 | 1 | 1 | 1 | 1 | 1 | 1 |
| ACT | Chlorpheniramine | 1 | — | — | — | — | — | — |
| | Nicotine | — | 0.2 | — | — | — | — | — |
| | Oxytocin | — | — | 0.001 | — | — | — | — |
| | Prednisone | — | — | — | 5 | — | — | — |
| | Desmopressin | — | — | — | — | 0.01 | — | — |
| | Diphenhydramine | — | — | — | — | — | 0.5 | — |
| | Benzydaminhydrochlorid | — | — | — | — | — | — | 0.5 |

TABLE 1B

Oral tablet compositions for bi-layer tablets containing active ingredients. Amount are given in wt-% of the respective layer of tablet.

| | | Ex. 8 | Ex. 9 | Ex. 10 | Ex. 11 | Ex. 12 | Ex. 13 | Ex. 14 |
|---|---|---|---|---|---|---|---|---|
| First layer (wt %) | Non-DC Erythritol | 50 | 50 | 50 | 50 | 50 | 50 | 50 |
| | DC Isomalt | 43.75 | 43.75 | 43.75 | 43.75 | 43.75 | 43.75 | 43.75 |
| | Flavor | 4 | 4 | 4 | 4 | 4 | 4 | 4 |
| | HIS | 0.25 | 0.25 | 0.25 | 0.25 | 0.25 | 0.25 | 0.25 |
| | Magnesium Stearate | 1 | 1 | 1 | 1 | 1 | 1 | 1 |
| | Binder HPC | 1 | 1 | 1 | 1 | 1 | 1 | 1 |
| Second layer (wt %) | DC Maltitol | — | — | — | — | — | — | — |
| | DC Xylitol | 93.75 | 94.55 | 94.749 | 89.75 | 94.74 | 94.25 | 94.25 |
| | DC Isomalt | — | — | — | — | — | — | — |
| | Flavor | 4 | 4 | 4 | 4 | 4 | 4 | 4 |
| | HIS | 0.25 | 0.25 | 0.25 | 0.25 | 0.25 | 0.25 | 0.25 |
| | Magnesium Stearate | 1 | 1 | 1 | 1 | 1 | 1 | 1 |
| ACT | Chlorpheniramine | 1 | — | — | — | — | — | — |
| | Nicotine | — | 0.2 | — | — | — | — | — |
| | Oxytocin | — | — | 0.001 | — | — | — | — |
| | Prednisone | — | — | — | 5 | — | — | — |
| | Desmopressin | — | — | — | — | 0.01 | — | — |
| | Diphenhydramine | — | — | — | — | — | 0.5 | — |
| | Benzydaminhydrochlorid | — | — | — | — | — | — | 0.5 |

TABLE 1C

Oral tablet compositions for bi-layer tablets containing active ingredients.
Amount are given in wt-% of the respective layer of tablet.

| | | Ex. 15 | Ex. 16 | Ex. 17 | Ex. 18 | Ex. 19 | Ex. 20 | Ex. 21 |
|---|---|---|---|---|---|---|---|---|
| First layer (wt %) | Non-DC Erythritol | 50 | 50 | 50 | 50 | 50 | 50 | 50 |
| | DC Isomalt | 43.75 | 43.75 | 43.75 | 43.75 | 43.75 | 43.75 | 43.75 |
| | Flavor | 4 | 4 | 4 | 4 | 4 | 4 | 4 |
| | HIS | 0.25 | 0.25 | 0.25 | 0.25 | 0.25 | 0.25 | 0.25 |
| | Magnesium Stearate | 1 | 1 | 1 | 1 | 1 | 1 | 1 |
| | Binder HPC | 1 | 1 | 1 | 1 | 1 | 1 | 1 |
| Second layer (wt %) | DC Maltitol | — | — | — | — | — | — | — |
| | DC Xylitol | — | — | — | — | — | — | — |
| | DC Isomalt | 93.75 | 94.55 | 94.749 | 89.75 | 94.74 | 94.25 | 94.25 |
| | Flavor | 4 | 4 | 4 | 4 | 4 | 4 | 4 |
| | HIS | 0.25 | 0.25 | 0.25 | 0.25 | 0.25 | 0.25 | 0.25 |
| | Magnesium Stearate | 1 | 1 | 1 | 1 | 1 | 1 | 1 |
| ACT | Chlorpheniramine | 1 | — | — | — | — | — | — |
| | Nicotine | — | 0.2 | — | — | — | — | — |
| | Oxytocin | — | — | 0.001 | — | — | — | — |
| | Prednisone | — | — | — | 5 | — | — | — |
| | Desmopressin | — | — | — | — | 0.01 | — | — |
| | Diphenhydramine | — | — | — | — | — | 0.5 | — |
| | Benzydaminhydrochlorid | — | — | — | — | — | — | 0.5 |

TABLE 1D

Oral tablet compositions for bi-layer tablets containing active
ingredients. Amount are given in wt-% of the respective layer of tablet.

| | | Ex. 22 | Ex. 23 | Ex. 24 | Ex. 25 | Ex. 26 | Ex. 27 |
|---|---|---|---|---|---|---|---|
| First layer (wt %) | Non DC Erythritol | 50 | 50 | 50 | 50 | 50 | 50 |
| | DC Isomalt | 43.75 | 43.75 | 43.75 | 43.75 | 43.75 | 43.75 |
| | Flavor | 4 | 4 | 4 | 4 | 4 | 4 |
| | HIS | 0.25 | 0.25 | 0.25 | 0.25 | 0.25 | 0.25 |
| | Magnesium Sterate | 1 | 1 | 1 | 1 | 1 | 1 |
| | Binder HPC | 1 | 1 | 1 | 1 | 1 | 1 |
| Second layer (wt %) | DC Maltitol | 93.75 | 93.75 | 94.5 | 94.25 | 94.65 | 44.75 |
| | DC Xylitol | — | — | — | — | — | — |
| | DC Isomalt | — | — | — | — | — | — |
| | Flavor | 4 | 4 | 4 | 4 | 4 | 4 |
| | HIS | 0.25 | 0.25 | 0.25 | 0.25 | 0.25 | 0.25 |
| | Magnesium Stearate | 1 | 1 | 1 | 1 | 1 | 1 |
| ACT | Cetirizine | 1 | — | — | — | — | — |
| | Bromhexine | — | 1 | — | — | — | — |
| | Cetylpyridinium | — | — | 0.25 | — | — | — |
| | Chlorhexidin | — | — | — | 0.5 | — | — |
| | Amylmetacresol | — | — | — | — | 0.1 | — |
| | Paracetamol | — | — | — | — | — | 50 |

TABLE 1E

Oral tablet compositions for bi-layer tablets containing active ingredients.
Amount are given in wt-% of the respective layer of tablet.

| | | Ex. 28 | Ex. 29 | Ex. 30 | Ex. 31 | Ex. 32 | Ex. 33 |
|---|---|---|---|---|---|---|---|
| First layer (wt %) | Non DC Erythritol | 50 | 50 | 50 | 50 | 50 | 50 |
| | DC Isomalt | 43.75 | 43.75 | 43.75 | 43.75 | 43.75 | 43.75 |
| | Flavor | 4 | 4 | 4 | 4 | 4 | 4 |
| | HIS | 0.25 | 0.25 | 0.25 | 0.25 | 0.25 | 0.25 |
| | Magnesium Stearate | 1 | 1 | 1 | 1 | 1 | 1 |
| | Binder HPC | 1 | 1 | 1 | 1 | 1 | 1 |
| Second layer | DC Maltitol | — | — | — | — | — | — |
| | DC Xylitol | 93.75 | 93.75 | 94.5 | 94.25 | 94.65 | 44.75 |

TABLE 1E-continued

Oral tablet compositions for bi-layer tablets containing active ingredients.
Amount are given in wt-% of the respective layer of tablet.

|  |  | Ex. 28 | Ex. 29 | Ex. 30 | Ex. 31 | Ex. 32 | Ex. 33 |
|---|---|---|---|---|---|---|---|
| (wt %) | DC Isomalt | — | — | — | — | — | — |
|  | Flavor | 4 | 4 | 4 | 4 | 4 | 4 |
|  | HIS | 0.25 | 0.25 | 0.25 | 0.25 | 0.25 | 0.25 |
|  | Magnesium Stearate | 1 | 1 | 1 | 1 | 1 | 1 |
| ACT | Cetirizine | 1 | — | — | — | — | — |
|  | Bromhexine | — | 1 | — | — | — | — |
|  | Cetylpyridinium | — | — | 0.25 | — | — | — |
|  | Chlorhexidin | — | — | — | 0.5 | — | — |
|  | Amylmetacresol | — | — | — | — | 0.1 | — |
|  | Paracetamol | — | — | — | — | — | 50 |

TABLE 1F

Oral tablet compositions for bi-layer tablets containing active ingredients.
Amount are given in wt-% of the respective layer of tablet.

|  |  | Ex. 34 | Ex. 35 | Ex. 36 | Ex. 37 | Ex. 38 | Ex. 39 |
|---|---|---|---|---|---|---|---|
| First layer (wt %) | Non DC Erythritol | 50 | 50 | 50 | 50 | 50 | 50 |
|  | DC Isomalt | 43.75 | 43.75 | 43.75 | 43.75 | 43.75 | 43.75 |
|  | Flavor | 4 | 4 | 4 | 4 | 4 | 4 |
|  | HIS | 0.25 | 0.25 | 0.25 | 0.25 | 0.25 | 0.25 |
|  | Magnesium Stearate | 1 | 1 | 1 | 1 | 1 | 1 |
|  | Binder HPC | 1 | 1 | 1 | 1 | 1 | 1 |
| Second layer (wt %) | DC Maltitol | — | — | — | — | — | — |
|  | DC Xylitol | — | — | — | — | — | — |
|  | DC Isomalt | 93.75 | 93.75 | 94.5 | 94.25 | 94.65 | 44.75 |
|  | Flavor | 4 | 4 | 4 | 4 | 4 | 4 |
|  | HIS | 0.25 | 0.25 | 0.25 | 0.25 | 0.25 | 0.25 |
|  | Magnesium Stearate | 1 | 1 | 1 | 1 | 1 | 1 |
| ACT | Cetirizine | 1 | — | — | — | — | — |
|  | Bromhexine | — | 1 | — | — | — | — |
|  | Cetylpyridinium | — | — | 0.25 | — | — | — |
|  | Chlorhexidin | — | — | — | 0.5 | — | — |
|  | Amylmetacresol | — | — | — | — | 0.1 | — |
|  | Paracetamol | — | — | — | — | — | 50 |

TABLE 1G

Oral tablet compositions for bi-layer tablets containing GI active
ingredients. Amount are given in wt-% of the respective layer of tablet.

|  |  | Ex. 40 | Ex. 41 | Ex. 42 | Ex. 43 | Ex. 44 | Ex. 45 |
|---|---|---|---|---|---|---|---|
| First layer (wt %) | Non DC Erythritol | 50 | 50 | 50 | 50 | 50 | 50 |
|  | DC Isomalt | 43.75 | 43.75 | 43.75 | 43.75 | 43.75 | 43.75 |
|  | Flavor | 4 | 4 | 4 | 4 | 4 | 4 |
|  | HIS | 0.25 | 0.25 | 0.25 | 0.25 | 0.25 | 0.25 |
|  | Magnesium Stearate | 1 | 1 | 1 | 1 | 1 | 1 |
|  | Binder HPC | 1 | 1 | 1 | 1 | 1 | 1 |
| Second layer (wt %) | DC Maltitol | 92.75 | 74.75 | 93.75 | 44.75 | 94.55 | 74.75 |
|  | DC Xylitol | — | — | — | — | — | — |
|  | DC Isomalt | — | — | — | — | — | — |
|  | Flavor | 4 | 4 | 4 | 4 | 4 | 4 |
|  | HIS | 0.25 | 0.25 | 0.25 | 0.25 | 0.25 | 0.25 |
|  | Magnesium Stearate | 1 | 1 | 1 | 1 | 1 | 1 |
| ACT | Omeprazole | 2 | — | — | — | — | — |
|  | Ibuprofen | — | 20 | — | — | — | — |
|  | Ondansetron | — | — | 1 | — | — | — |
|  | Paracetamol (Acetaminophen) | — | — | — | 50 | — | — |
|  | Loperamidhydrochlorid | — | — | — | — | 0.2 | — |
|  | Rantidine | — | — | — | — | — | 20 |

TABLE 1H

Oral tablet compositions for bi-layer tablets containing GI active ingredients. Amount are given in wt-% of the respective layer of tablet.

| | | Ex. 46 | Ex. 47 | Ex. 48 | Ex. 49 | Ex. 50 | Ex. 51 |
|---|---|---|---|---|---|---|---|
| First layer (wt %) | Non DC Erythritol | 50 | 50 | 50 | 50 | 50 | 50 |
| | DC Isomalt | 43.75 | 43.75 | 43.75 | 43.75 | 43.75 | 43.75 |
| | Flavor | 4 | 4 | 4 | 4 | 4 | 4 |
| | HIS | 0.25 | 0.25 | 0.25 | 0.25 | 0.25 | 0.25 |
| | Magnesium Stearate | 1 | 1 | 1 | 1 | 1 | 1 |
| | Binder HPC | 1 | 1 | 1 | 1 | 1 | 1 |
| Second layer (wt %) | DC Maltitol | — | — | — | — | — | — |
| | DC Xylitol | 92.75 | 74.75 | 93.75 | 44.75 | 94.55 | 74.75 |
| | DC Isomalt | — | — | — | — | — | — |
| | Flavor | 4 | 4 | 4 | 4 | 4 | 4 |
| | HIS | 0.25 | 0.25 | 0.25 | 0.25 | 0.25 | 0.25 |
| | Magnesium Stearate | 1 | 1 | 1 | 1 | 1 | 1 |
| ACT | Omeprazole | 2 | — | — | — | — | — |
| | Ibuprofen | — | 20 | — | — | — | — |
| | Ondansetron | — | — | 1 | — | — | — |
| | Paracetamol (Acetaminophen) | — | — | — | 50 | — | — |
| | Loperamidhydrochlorid | — | — | — | — | 0.2 | — |
| | Rantidine | — | — | — | — | — | 20 |

TABLE 1I

Oral tablet compositions for bi-layer tablets containing GI active ingredients. Amount are given in wt-% of the respective layer of tablet.

| | | Ex. 52 | Ex. 53 | Ex. 54 | Ex. 55 | Ex. 56 | Ex. 57 |
|---|---|---|---|---|---|---|---|
| First layer (wt %) | Non DC Erythritol | 50 | 50 | 50 | 50 | 50 | 50 |
| | DC Isomalt | 43.75 | 43.75 | 43.75 | 43.75 | 43.75 | 43.75 |
| | Flavor | 4 | 4 | 4 | 4 | 4 | 4 |
| | HIS | 0.25 | 0.25 | 0.25 | 0.25 | 0.25 | 0.25 |
| | Magnesium Stearate | 1 | 1 | 1 | 1 | 1 | 1 |
| | Binder HPC | 1 | 1 | 1 | 1 | 1 | 1 |
| Second layer (wt %) | DC Maltitol | — | — | — | — | — | — |
| | DC Xylitol | — | — | — | — | — | — |
| | DC Isomalt | 92.75 | 74.75 | 93.75 | 44.75 | 94.55 | 74.75 |
| | Flavor | 4 | 4 | 4 | 4 | 4 | 4 |
| | HIS | 0.25 | 0.25 | 0.25 | 0.25 | 0.25 | 0.25 |
| | Magnesium Stearate | 1 | 1 | 1 | 1 | 1 | 1 |
| ACT | Omeprazole | 2 | — | — | — | — | — |
| | Ibuprofen | — | 20 | — | — | — | — |
| | Ondansetron | — | — | 1 | — | — | — |
| | Paracetamol (Acetaminophen) | — | — | — | 50 | — | — |
| | Loperamidhydrochlorid | — | — | — | — | 0.2 | — |
| | Rantidine | — | — | — | — | — | 20 |

TABLE 1J

Oral tablet compositions for bi-layer tablets containing active ingredients. Amount are given in wt-% of the respective layer of tablet.

| First layer (wt %) | Ex. 58 | Ex. 59 | Ex. 60 | Ex. 61 | Ex. 62 |
|---|---|---|---|---|---|
| Non-DC Erythritol | 50 | 50 | — | 45 | 45 |
| DC Isomalt | 36.85 | 40.03 | 83.03 | 33.88 | 44.15 |
| DC CaCO3 | — | — | 7 | 16.27 | 7 |
| Caffeine | 6.35 | 3.17 | 3.17 | — | — |
| Flavor | 4.45 | 4.45 | 4.45 | 1.5 | 1.5 |
| HIS | 0.35 | 0.35 | 0.35 | 0.35 | 0.35 |
| Magnesium Stearate | 1 | 1 | 1 | 1 | 1 |
| Binder HPC | 1 | 1 | 1 | 2 | 1 |

| Second layer (wt %) | Energy 75 mg Caffeine-total tablet | Energy 75 mg Caffeine-total tablet | Energy 75 mg Caffeine-total tablet | Anti-acid 250 mg CaCO3-total tablet | Anti-acid 600 mg CaCO3-total tablet |
|---|---|---|---|---|---|
| DC Xylitol | 92.22 | 89.59 | 82.04 | 86.44 | 38.28 |
| DC CaCO3 | — | — | 7 | 11.51 | 59.67 |
| Caffeine | 1.98 | 5.16 | 5.16 | — | — |
| Flavor | 4.45 | 4 | 4.45 | 1 | 1 |
| HIS | 0.35 | 0.25 | 0.35 | 0.05 | 0.05 |
| Magnesium Stearate | 1 | 1 | 1 | 1 | 1 |

The compositions indicated in the above Tables 1A, 1B, 1C, 1D, 1E, 1F, 1G, 1H, 1I and 1J are each processed into two-layer tablets with compositions as outlined in examples 1-62

For each example 1-62 the raw materials are sieved with a 1600 micron sieve and then weighed into the proper amount according to the exampled compositions of Tables 1A to 1I.

For each layer the weighed amounts are then added to a Turbula mixer in a stainless steel container and blended at 50 rpm for 5 minutes. MgSt was added after 4 minutes of blending.

It is noted that the active ingredient ACT is present in the second layer in all examples. It should be noted that the seven exemplified buccal active ingredients are in no way limiting and it is also noted that it is possible to administer the active ingredients via the first layer. The shown way of administering the active ingredient via the second layer, i.e. the layer not containing the non-DC sugar alcohol, represents a very advantageous design in terms of the desired technical effect. It is also noted that each tablet may also contain more than one active ingredient and it is also noted that different active ingredients in that case may be distributed in different layers. It is also noted that more than two layers may also be applied within the scope of the invention, and one advantageous design e.g. may include two layers, a first and a second layer as specified herein but now added with an intermediate layer comprising one of the applied active ingredients. It should also be noted that the term layer in relation to the present embodiment may elsewhere in this application be referred to as a module. In terms of active ingredients, it is noted that some active ingredients may advantageously be applied on a tablet which is not multimodular.

The mixtures are then tableted by means of a Piccola RIVA DC-SC-041-2 or a Fette 3090i.

The applied molds have circular cross sections with diameters of 16 mm and are hollowed to produce tablets, which are concave and/or curved. Evidently, other mold size and shapes may be applied within the scope of the invention.

The resulting tablets according to Examples 1-62 are then obtained by tableting with a suitable pressure force.

For each tablet of examples 1-62, the second layer as outlined in the above table is pressed initially at a first relatively low pressure. The blended composition of the so-called first layer is then fed to the mold and a final two-layer tablet is then compressed at higher pressure than the pressure applied on the first layer, thereby producing final two-layer tablets according to Examples 1-62 It is noted that the final two-layer tablets of examples 1-62 are 1.8 gram tablets and that the first layer of the tablets weighs 0.9 and the second layer of the tablets weighs 0.9 gram.

A specification of relevant compounds applied in the examples explained above are listed below.

HPC: Hydroxy propyl cellulose. Klucel Nutra D from Ashland

Non DC Erythritol: Zerose 16952 from Cargill

DC Xylitol—Xylitab 200 from Dupont

DC Isomalt—Isomalt DC 101 from Beneo Paltinit

DC Maltitol—Sweetpearl 300 DC from Roquette

The above two-layer Examples 1-62 were evaluated according to mechanical strength and the important salivation was evaluated as explained with reference to FIG. 7.

It was noted that the use of DC maltitol, DC Xylitol and DC Isomalt in the second layers of the examples were regarded sufficient and an attractive means for carrying the respective active ingredients from a mechanical perspective, which is important due to the fact that the high load of non-DC-sugar alcohol in the first layer will weaken the first layer.

In terms of the salivation effect, it is noted that the swallowability is promoted through the use of the non-DC sugar alcohols. To many users swallowing of an oral tablet containing an active ingredient is difficult or impossible and the intended administration of the active ingredient in question is considered extremely difficult. It is also noted that fast melting tablets are often equally difficult and unpleasant for a user. The present chewable tablets are increasing the ability of a user to get the benefit of the active ingredient as the inventive oral tablet promotes salivation to a degree that makes the user able to accept swallowing the active ingredient when the tablet is masticated and the active ingredient is in the mouth. The motivation for swallowing the masticated oral tablet is greatly increased by the use of the non-DC sugar alcohol.

It is in particular noted that the present evaluation in terms of swallowability is greatly concerned with the taste masking as the active ingredients of the examples are generally associated with a non-pleasant taste or user perception. This is exemplified in different aspects with Example 58-60 with caffeine and in another aspect with Examples 61-62 where CaCO3 are added.

In Examples 58-60, caffeine has been included in different amounts and distributed in both layers. It was noted according to this embodiment that it was possible to include the active ingredient in both layers although the second layer may be preferred in some embodiments. From a taste masking angle, it was established that the tablets of Ex. 58-60 provided a more pleasant mouth sensation in terms of complete mouthfeel. The test panel noted that well-known parameters used within the art were not sufficient to describe the overall impression of the tablet, but it was clear, when compared with a reference tablet with the same composition but where non-DC erythritol in the first layer had been exchanged with DC-erythritol, that the tablets of Examples 58-60 were far superior in terms of perception.

The very distinguished taste of caffeine was still noted by the test panel but the overall impression was far better than the comparative DC-based reference in terms of complete mouthfeel and the taste was, although perceived, accepted as being taste masked. The taste masking perceived was both referred to salivation but also to the disintegration and dissolving of the tablet during mastication. Overall, the caffeine tablets made according to the provisions of the invention were deemed very attractive.

An alternative, also potentially non-pleasant compound were processed according to Example 61 and 62, where substantial amount of CaCO3 were added to the tablet and evaluated. Example 61 in particular were deemed acceptable and with a nice taste during mastication and swallowing even though CaCO3 from a user perspective may conventionally be perceived very non-pleasant when chewing.

Again, the DC-erythritol and the associated improved salivation were pointed at as the reason for the obtained taste masking of the chalky tasting CaCO3.

Figure 7:
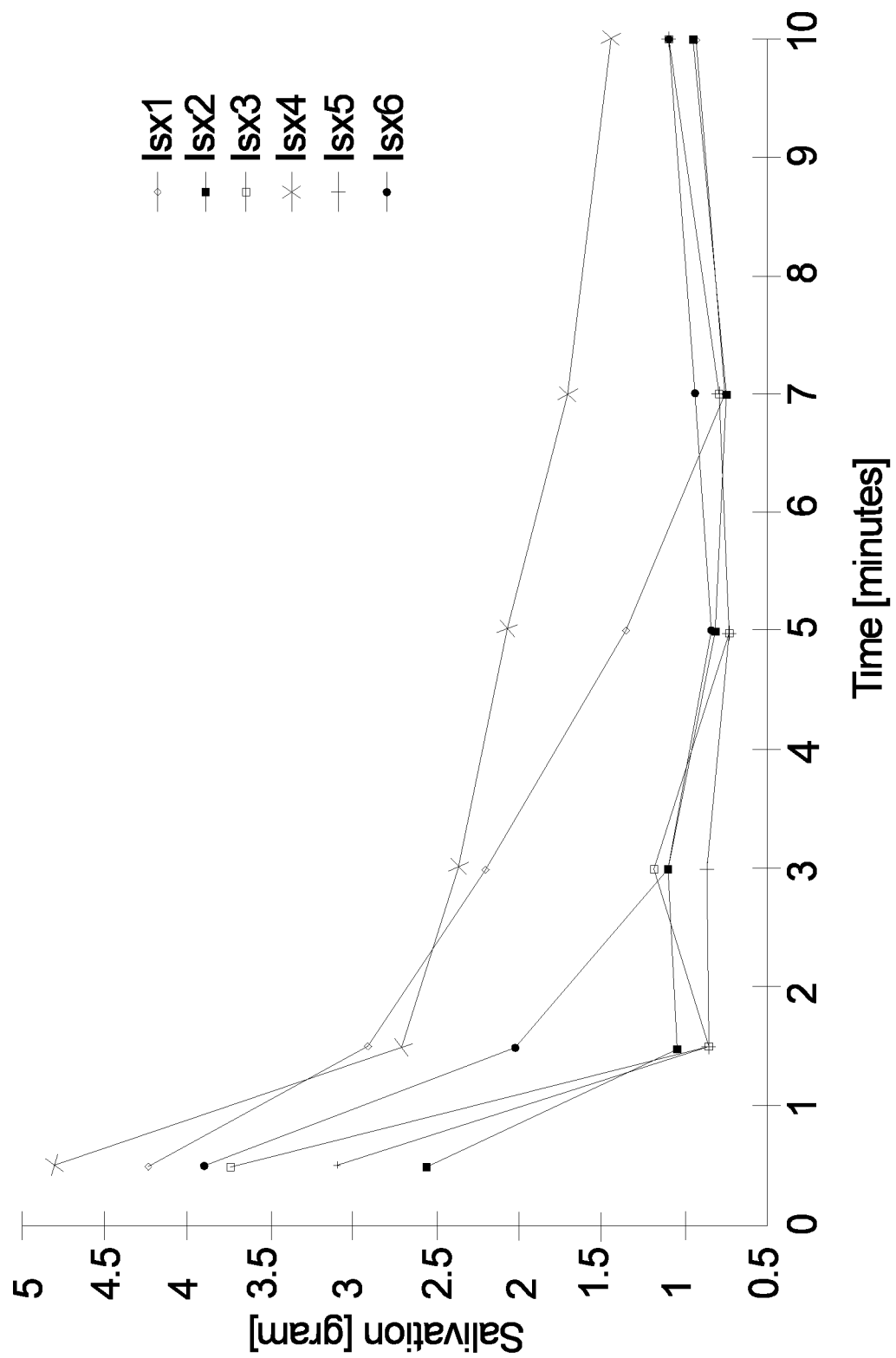
FIG. 7 illustrates the short and long-term effect of salivation obtained through different types of non-DC sugar alcohols.

FIG. 7 illustrates a measuring of the salivation effect related to the above-mentioned Example 9 in different variants, where different non-DC sugar alcohols have been applied in a tablet according to Example 9 without an active ingredient and where the non-DC sugar alcohol has been exchanged with alternatives to the non-DC erythritol applied in Example 9 as specified below. Sorbitol is applied as a reference, representative DC sugar alcohol.

ISX1 refers to a non-DC xylitol variant of Example 9 with same amount of non-DC sugar alcohol,
ISX2 refers to a non-granulated sorbitol variant of Example 9 with same amount of non-DC sugar alcohol,
ISX3 refers to a non-DC isomalt variant of Example 9 with same amount of non-DC sugar alcohol,
ISX4 refers to a non-DC erythritol corresponding to Example 9,
ISX5 refers to a non-DC mannitol variant of Example 9 with same amount of non-DC sugar alcohol and
ISX6 refers to a non-DC maltitol variant of Example 9 with same amount of non-DC sugar alcohol.

The saliva generation as measured with reference to FIG. 7 and the associated examples is defined in the description as a definition with reference to the measuring method.

The results of the measured saliva generation are illustrated in FIG. 7, where saliva generation in measured in grams as a function of time (minutes).

It is noted that the saliva generation from all non-DC sugar alcohols are impressive in the beginning, but it is also noted that saliva generation over time is no less than astonishing in relation to ISX4, i.e. the non-DC erythritol example 9. It is thus noted that the salivation effect is increased a very long time after the major part of non-DC erythritol based tablet has been swallowed or collected during the measurement. The obtained salivation effect is believed to at least be a part of the non-DC sugar alcohols ability in promotion of the obtained taste masking.

What is claimed is:

1. An oral direct compression tablet for taste masking of active ingredients, the tablet comprising a population of particles and an active ingredient with off-note taste, the population of particles comprising directly compressible (DC) and non-directly compressible (non-DC) sugar alcohol particles, the non-DC particles consisting essentially of pure non-DC sugar alcohol, the non-DC particles providing the direct compression tablet with a plurality of discrete non-DC areas formed by single non-DC particles or small groups of non-DC particles distributed between the DC particles, and the non-DC areas resulting at least partly in induced taste masking upon mastication of the tablet, wherein said active ingredient with off-note taste is selected from the group consisting of an active ingredient with bitter taste, an active ingredient with metallic taste, an active ingredient with astringent taste, an active ingredient with chalky taste, an active ingredient with salty taste, and combinations thereof.

2. An oral direct compression tablet for taste masking of active ingredients, the tablet comprising a population of particles and an active ingredient with off-note taste, the population of particles comprising directly compressible (DC) and non-directly compressible (non-DC) sugar alcohol particles, the non-DC particles consisting essentially of pure non-DC sugar alcohol, the non-DC particles providing the direct compression tablet with a plurality of discrete non-DC areas distributed between the DC particles, and the non-DC areas resulting at least partly in induced taste masking of the active ingredient upon mastication of the tablet, wherein said active ingredient with off-note taste is selected from the group consisting of an active ingredient with bitter taste, an active ingredient with metallic taste, an active ingredient with astringent taste, an active ingredient with chalky taste, an active ingredient with salty taste, and combinations thereof.

3. The tablet according to claim 2, wherein the tablet comprises said non-DC sugar alcohol particles in an amount of at least 10% by weight of the tablet.

4. The tablet according to claim 2, wherein at least 30% by weight of the non-DC sugar alcohol particles have a particles size above 500 μm.

5. The tablet according to claim 2, wherein the tablet has a weight ratio between said non-DC sugar alcohol particles and said DC sugar alcohol particles, which is between 0.3 and 0.7.

6. The tablet according to claim 2, wherein the non-DC sugar alcohol particles are selected from non-DC particles of erythritol, maltitol, mannitol, xylitol, lactitol, isomalt, and combinations thereof.

7. The tablet according to claim 2, wherein the tablet is a chewable tablet.

8. The tablet according to claim 2, wherein said active ingredient with off-note taste is an analgesic selected from the group consisting of ibuprofen, acetaminophen, dextromethorphan, ampicillin, clarithromycin, metronidazole, loperamide, caffeine, sumatriptan, ascorbic acid, and combinations thereof.

9. The tablet according to claim 2, wherein said active ingredient with off-note taste is an antihistamine selected from the group consisting of cimetidine, ranitidine, famotidine, nizatidine, desloratadine, and combinations thereof.

10. The tablet according to claim 2, wherein said active ingredient with off-note taste is a gastrointestinal active selected from the group consisting of omeprazole, ondansetron, loperamide, simethicone, calcium carbonate, metoclopramide, cisapride, docusate, and combinations thereof.

11. The tablet according to claim 2, wherein said active ingredient with off-note taste is selected from vitamins, minerals, supplements, and combinations thereof.

12. The tablet according to claim 2, wherein said active ingredient with off-note taste is a hormone selected from the group consisting of progesterone, testosterone, melatonin, and combinations thereof.

13. The tablet according to claim 2, wherein said active ingredient with off-note taste is a zinc salt selected from the group consisting of zinc acetate, zinc chloride, zinc gluconate, and combinations thereof.

14. The tablet according to claim 2, wherein said population of particles is tableted into a first module and combined with a second population of particles that is tableted into a second module.

15. The tablet according to claim 2, wherein said population of particles is tableted into a first module and combined with a second population of particles that is tableted into a second module, wherein the second population of particles includes particles comprising gum base.

16. The tablet according to claim 2, wherein said population of particles is tableted into a first module together with particles comprising gum base and combined with a second population of particles that is tableted into a second module.

17. An oral tablet for taste masking of active ingredients, the tablet comprising a population of particles and an active ingredient with off-note taste, the population of particles comprising directly compressible (DC) and non-directly compressible (non-DC) sugar alcohol particles, the non-DC particles consisting essentially of pure non-DC sugar alcohol, the non-DC particles providing the tablet with a plurality of discrete non-DC areas distributed between the DC particles, and the non-DC areas resulting at least partly in induced taste masking of the active ingredient upon mastication of the tablet, wherein said active ingredient with off-note taste is selected from the group consisting of an active ingredient with bitter taste, an active ingredient with metallic taste, an active ingredient with astringent taste, an active ingredient with chalky taste, an active ingredient with salty taste, and combinations thereof.

18. The tablet according to claim 17, wherein said active ingredient with off-note taste is selected from active ingredients for the throat selected from the group consisting of acetylcysteine, ambroxol, amylmetacresol, benzocaine, bisacodyl, bismuth subsalicylate, bromhexine, cetirizine, cetylpyridinium, chlorhexidine, dextromethorphan hydrobromide, 2,4-dichlorobenzyl alcohol, doxylamine succinate, eucalyptus oil, flurbiprofen, glycerin, hexylresorcinol, lidocaine, menthol, myrrh, paracetamol, pectin, peppermint oil, phenol, phenylephrine, povidone-iodine, pseudoephedrine, ranitidine, simethicone, sodium docusate, spearmint, zinc, and any combination thereof; active ingredients for the gastrointestinal tract selected from the group consisting of alginate, atenolol, aspirin (acetylsalicylic acid), ampicillin, aminosalicylates, anhydrous citric acid, bisacodyl, bismuth subsalicylate, bupropion, caffeine, calcium, calcium carbonate, cetirizine, cimetidine, cisapride, clarithromycin, desloratadine, dexlansoprazole, diphenhydramine HCl, diphenhydramine citrate, dimenhydrinate, docusate erythromycin, dopamine, esomeprazole, famotidine, fexofenadine HCl, guaifenesin, hydrotalcite, ibuprofen, ketoprofen, lactase enzyme, lansoprazole, loratadine, lorcaserin, loperamide, loperamide HCl, magnesium, magnesium carbonate, magnesium hydroxide, melatonin, methamphetamine HCl, metoclopramide, metronidazole, montelukast, mycostatin, naltrexone, naproxen, naproxen sodium, nizatidine, omeprazole, ondansetrone, orlistat, pantoprazole, paracetamol (acetaminophen), pectin, phentermine HCl, polypodium leucotomos, prednisolone, prednisone, progesterone, propranolol, propantheline bromide, pseudoephedrine HCl, phentermine, rabeprazole, ranitidine, roflumilast, scopoloamine butyl hydroxide, simethicone, sodium, sodium bicarbonate, sodium docusate, sumatriptan, testosterone, tetracycline, topiramate, vitamin A, vitamin B, vitamin B12, vitamin C (ascorbic acid), vitamin D, and vitamin E, vitamin K, and any combination thereof, and active ingredients for buccal absorption selected from the group consisting of atenolol, baclofene, caffeine, carvedilol, chlorpheniramine, chlorpheniramine maleate, fluticasone propionate, maleate, desmopressine, diltiazem hydrochloride, doxylamine succinate, mycostatin, nicotine, nifedipine, nitroglycerin, omeprazole, ondansetrone, oxymetazoline HCl, oxytocin, phenylephrine, piroxicam, prednisone, propranolol, salbutamol sulphate, scopoloamine butyl hydroxide, sumatriptan, triamcinolonacetonid, and any combination thereof.

* * * * *